United States Patent [19]

Posner et al.

[11] Patent Number: 5,614,371
[45] Date of Patent: Mar. 25, 1997

[54] RI FUSION ANTIGEN RECOGNIZED BY ANTIBODIES ASSOCIATED WITH PARANEOPLASTIC OPSOCLONUS AND METHODS OF USE THEREOF

[75] Inventors: Jerome B. Posner; Robert B. Darnell; Henry M. Furneaux, all of New York, N.Y.

[73] Assignee: Sloan-Kettering Institute for Cancer Research, New York, N.Y.

[21] Appl. No.: 187,793

[22] Filed: Jan. 26, 1994

Related U.S. Application Data

[63] Continuation of Ser. No. 691,559, Apr. 25, 1991, abandoned.

[51] Int. Cl.$^6$ .................. G01N 33/579; C07K 14/47; C07K 19/00; C07K 14/705
[52] U.S. Cl. .................. 435/7.23; 424/185.1; 424/277.1; 435/7.1; 435/69.7; 435/7.9; 436/64; 436/536; 436/542; 530/350; 530/403; 530/828
[58] Field of Search ............... 424/277.1, 185.1; 530/350, 403, 828; 435/7.1, 7.23, 69.7, 7.9; 436/536, 542, 64

[56] References Cited

FOREIGN PATENT DOCUMENTS 0297585  1/1989  European Pat. Off. ........ C12N 15/00

OTHER PUBLICATIONS

Bowie et al. Science 247:1306–1310 1990.
Furneaux, H.F. et al. Neurology 40:1085–1091. 1990.
Furneaux, H.F. et al. Proc. Natl. Acad. Sci USA 1990 86:2873–2877.
Dropcho, E.J. et al. Proc. Natl. Acad. Sci USA 84:4552–4556. 1987.
Korngreth, S.E. et al. Cancer Res. 46:2588–2595. 1986.
Ruddle–Steffen, C. et al. Ann. Neurol. 23:528–531. (abstract only) 1988.
Luque, F.A. et al. Ann. Neurol. 29:241–251. 1991.
Fathallah–Shaykh, H. et al. Proc. Natl. Acad. Sci USA 88:3451–3454. 1991.
Sakai, K. et al. Ann. Neurol. 28:692–698. 1990.
Furneaux, H.M. et al. New Engl. J. Med. 322:1844–1851.

*Primary Examiner*—Lila Feisee
*Assistant Examiner*—Anthony C. Caputa
*Attorney, Agent, or Firm*—John P. White

[57] ABSTRACT

An isolated nucleic acid sequence encoding Ri paraneoplastic antigenic polypeptide is provided by this invention. This invention also provides a purified Ri antigenic polypeptide and compositions containing the purified Ri antigenic polypeptide. Further provided by this invention is a antibody directed to an epitope on the Ri paraneoplastic antigenic polypeptide. Compositions containing this antibody also are provided by this invention. This invention also provides methods of diagnosis and treatment using the compositions described hereinabove.

6 Claims, 20 Drawing Sheets

Figure 5A

```
CCAGATGATCCAGATCGCATCAAACAAGTAAAG
 P  D  D  P  D  R  I  K  Q  V  K

ATTATAGTTCCAACAGCACAGCAGGTCTGATA
 I  I  V  P  N  S  T  A  G  L  I

ATAGGGAAGGGAGGTGCTACTGTGAAGGCTGTA
 I  G  K  G  G  A  T  V  K  A  V

ATGGAGCAGTCAGGGGCTTGGGTGCAGCTT
 M  E  Q  S  G  A  W  V  Q  L

TCCCAGAAACCTGATGGGATCAACTTGCAAGAG
 S  Q  K  P  D  G  I  N  L  Q  E

AGGGTTGTCACTGTGAGTGGAGAACCTGAACAA
 R  V  V  T  V  S  G  E  P  E  Q

AACCGAAAAGCTGTTGAACTTATCATCCAGAAG
 N  R  K  A  V  E  L  I  I  Q  K

ATACAAGAGGATCCACAAAGTGGCAGCTGTCTC
 I  Q  E  D  P  Q  S  G  S  C  L

AATATCAGTTATGCCAATGTGACAGGTCCAGTG
 N  I  S  Y  A  N  V  T  G  P  V
```

Figure 5B

```
GCAAATTCCAATCCAACCGGATCTCCTTAT
 A   N   S   N   P   T   G   S   P   Y

GCAAACACTGCTGAAGTGTTACCAACTGCTGCA
 A   N   T   A   E   V   L   P   T   A   A

GCAGCTGCAGGGCTATTAGGACATGCTAACCTT
 A   A   A   G   L   L   G   H   A   N   L

GCTGGCGTTGCAGCCTTTCCAGCAGTTTTATCT
 A   G   V   A   A   F   P   A   V   L   S

GGCTTCACAGGCAATGACCTGGTGGCCATCACC
 G   F   T   G   N   D   L   V   A   I   T

TCTGCACTTAATACATTAGCCAGCTATGGATAT
 S   A   L   N   T   L   A   S   Y   G   Y

AATCTCAACACTTTAGGTTTAGGTCTCAGT
 N   L   N   T   L   G   L   G   L   S
```

Figure 5C

```
CAAGCAGCAGCAACAGGGGCTTTGGCTGCAGCA
 Q  A  A  A  T  G  A  L  A  A  A

GCTGCCAGTGCCAACCCAGCAGCAGCAGCAGCC
 A  A  S  A  N  P  A  A  A  A  A

AATTTATTGGCCACCTATGCCAGTGAAGCCTCA
 N  L  L  A  T  Y  A  S  E  A  S

GCCAGTGGCAGCACAGCTGGTGGTACGGCGGGG
 A  S  G  S  T  A  G  G  T  A  G

ACATTTGCATTAGGTAGCCTGGCTGCTGCTACT
 T  F  A  L  G  S  L  A  A  A  T

GCTGCAACCAATGGATATTTTGGAGCTGCT
 A  A  T  N  G  Y  F  G  A  A

TCTCCCCTAGCTGCCAGTGCCATTCTAGGAACA
 S  P  L  A  A  S  A  I  L  G  T

GAAAAGTCCACAGATGGATCCAAGGATGTAGTT
 E  K  S  T  D  G  S  K  D  V  V

GAAATAGCAGTGCCAGAAAACTTAGTTGGTGCA
 E  I  A  V  P  E  N  L  V  G  A

ATACTTGGCAAAGGAGGGAAAACATTAGTGGAA
 I  L  G  K  G  G  K  T  L  V  E
```

Figure 5D

```
TACCAGGAGTTGACTGGTCAAGGATACAGATC
 Y  Q  E  L  T  G  A  R  I  Q  I

TCCAAAAAAGGAGAATTCGTACCTGGCACA
 S  K  K  G  E  F  V  P  G  T

AGGAATCGGAAGGTAACCATTACTGGAACACCA
 R  N  R  K  V  T  I  T  G  T  P

GCTGCAACACAGGCTGCTCAATATTTAATTACA
 A  A  T  Q  A  A  Q  Y  L  I  T

CAAAGGATCACATATGAGCAAGGAGTTCGGGCT
 Q  R  I  T  Y  E  Q  G  V  R  A

GCCAATCCTCAGAAAGTGGGTTGAGTGCCCCA
 A  N  P  Q  K  V  G  *

GTTACACATCAGATTGTTTTAACCCCTCCTTTA
CCCCATTTTCAAGAAGGATGTACTGTACTTTG
CAGAAGTGAAGTTTTTCTGTTATTAATATATAA
TTATGCAAATGAATGCGACTATGTTGACAATG
TGTATATGTAAATAATATGTGTTTTACCAGAT
GTTTCATAGAAGAATTTTTTCTTGATCTGTTT
TGTTCTCTATACTTTGCTTGTGTATATTTGTC
AGAGGTGTTTCTAGTGTAAGATTTAAGCCTGCC
ATTTTACCAGCATTATTGTAGTTTAATGATTG
AATGTAGACAGGGATATGCGTATAGTTTTCAGT
ATTAGTTCTAGATAACACTAAATTAACTACTGT
TAGGTTGAGTATGGTGGGGTCAGTGACCTAAA
ATGGAGTGAGGCCAAAGCACTGTCCTGTAAGT
CTTACTTCCTGCTTAGGGCACAGTGAAGTAGGA
```

Figure 5E

```
AACAATATTTTGAAAATAAGTTTTAAATTTAA
AATGATCAAAAAGCAATATAGTTGCATAAAAGC
ACTGTAAATATTTAAAAGGTTAAAACTGTGGA
AAATTATATTGGTAAGTTTACAGATCAATAAA
AGCACCTGTTCTCCATCTGAACTAGACAATGG
AAATAATGCTGCATGCTGCCATGGCCCATTCTT
CATCATTTGTAAGTTCAACAAAGTTCTCACAT
GGAGTCCCACCTCTTCAGAGGTTGCACATTTG
TTTTTAAGACTGAATTCACTACTGATCCCATCG
CCTGGCCGAGACAGTCATTACTCCATTAACAT
CCTACTGTTAGACACATAACTGTGGTACAGGA
TTGGAAATTATAAACAAAGTGAAGTGCCAACA
AATTATTGATAGCTGATAATGTTTCATATCTG
CAACTGCTTGATAAGTATGTTGCATTTTAAGAG
CTATAATTGTGTATAATTTGTTAACACTAGAA
ACCTATTAGTATTGTGAATGTAGATTTTACTGT
GAAGCTATCTGTGATTTAGCTGTTTGCTCCCA
TGATGGAGTCTTTGCAGCATGGCGCTAGCAGCC
AATGCAGTTTCTATACTCGGTAATTTGCATGT
TTTGTGGAGCATTTTTATGTCACCAACCAGACA
GTATTTCCTGCATGCTTATTTAGAAGAGGCAGC
TTATCTTGAGAGGTAGTGTTATCTACCTTTGT

CAGGCTTTTTTGACAGGTCATTTCAGAGTAAGC
CTTTGTTCCCAAGACCCAACAACTGTCACCCTC
TTCTGTACCTCTCCTGAGTGCCAACTGTCCAG
GCCATTTGACACACCATCTGTTAACCTCTGAGT
TTGCCCACTCAAGGCCACTCATAGGGGCATCC
TAGCCCTGTGCACTCAGCACTCATAGGATCATC
CAGACTCTCATGCGGCATGCAGTCTAATCATG
ACAAATAATGCTGCTACTCTGATATCTGGCTGA
GCAACTGAATTACAAAGAGAATTACTTCCAT
CTCAACTTCAACCCATTGATTACGTCCATCCTA
GCAAGCTAAATGGCATCCCAGCTGCTCCTTTC
TGTGCAACCAATTAAAGAACAATGAGTGTGATG
CTCCATGTCTGAATTTCGTCCAGCCTCTCTCT
GAACTGTGATCTTTGTCCTCATGAACTTTCCCT
TTTGTTCATTGAACTATATGGACTCTTCATTT
CATATTGATTACTGTGCAATTTACTTTTGGACA
TTGAGAACTTGAAATTATTGGAATTC
```

Figure 7A

Hom #1

```
GAATTCCGACAAAACAAAGGGAGAACCTTCTCCCGGTAGCAGCG
 E  F  R  Q  N  K  R  E  N  L  L  P  V  A  A

GCAGGAACTGCAAACATGATGGCGCAGCTCCCATCCAGCAGAAC
 A  G  T  A  N  M  M  A  A  A  P  I  Q  Q  N

GGGACCCCACACTGGGGTTCCCATAGACCTGGACCCGCCGGACTCG
 G  T  H  T  G  V  P  I  D  L  D  P  P  D  S

CGGAAAGGCCGCTGGAAGCCCCTGAAGCCCAGCACCAAG
 R  K  R  P  L  E  A  P  P  E  A  G  S  T  K

AGGACCAATACGGGCGAAGACGGCCAGTATTTCTAAAGGTTCTC
 R  T  N  T  G  E  D  G  Q  Y  F  L  K  V  L

ATACCCTAGTTATGCTGCTGGATCTCTATAATTGGGAAGGGAGGACAG
 I  P  S  Y  A  A  G  S  I  I  G  K  G  G  Q
```

Figure 7B

```
ACAATTGTTCAGTTGCAAAAGAAACTGGAGCCACCATCAAGCTG
 T  I  V  Q  L  Q  K  E  T  G  A  T  I  K  L
TCTAAGTCTAAGTCCAAAGATTTTACCCAGGTACTACTGAG
 S  K  L  S  K  S  K  D  F  Y  P  G  T  T  E
CGAGTGTGCTTGATCCAGGGAACGGTTGAAGCACTGAATGCAGTT
 R  V  C  L  I  Q  G  T  V  E  A  L  N  A  V
CATGGATTCATTGCAGAAAAAATTCGAGAAATGCCCCAAAATGTG
 H  G  F  I  A  E  K  I  R  E  M  P  Q  N  V
GCCAAGACAGAACCAGTCAGCATTCTACAACCCCAGACCACCGTT
 A  K  T  E  P  V  S  I  L  Q  P  Q  T  T  V
```

Hom #1

Figure 7C

```
        500
         *
AATCCAGATCGCATCAAACAAACATTGCCATCTTCCCAACTACC      EXON
 N  P  D  R  I  K  Q | T  L  P  S  S  P  T  T
ACCAAGTCCTCTCCATCTGATCCCATGACCACCTCCAGAGCTAAT
 T  K  S  S  P  S  D  P  M  T  T  S  R  A  N
CAGGTAAAGATTATAGTTCCCAACAGCACAGCAGGTCTGATAATA      Hom #2
 Q | V  K  I  I  V  P  N  S  T  A  G  L  I  I
GGGAAGGGAGGTGCTACTGTGAAGGCTGTAATGGAGCAGTCAGGG
 G  K  G  G  A  T  V  K  A  V  M  E  Q  S  G
GCTTGGGTGCAGCTTTCCCAGAAACCTGATGGGATCAACTTGCAA
 A  W  V  Q  L  S  Q | K  P  D  G  I  N  L  Q
GAGAGGGTTGTCACTGTGAGTGGAGAACCTGAACAAAACCGAAAA
 E  R  V  V  T  V  S  G  E  P  E  Q  N  R  K
GCTGTTGAACTTATCATCCAGAAGATACAAGAGGA
 A  V  E  L  I  I  Q  K  I  Q  E  D
```

Figure 7D

TCCACAAAGTGGCAGCTGTCTCAATATCAGTTATGCCAATGTGACA
P Q S G S C L N I S Y A N V T

GGTCCAGTGGCAAATTCCAATCCAACCGGATCTCCTTATGCAAAC
G P V A N S N P T G S P Y A N

ACTGCTGAAGTGTTACCAACTGCTGCAGCAGCTGCAGGGCTATTA
T A E V L P T A A A A A G L L

GGACATGCTAACCTTGCTGGCGTTGCAGCCTTTCCAGCAGTTTTA
G H A N L A G V A A F P A V L
              1000
               *

TCTGGCTTCACAGGCAATGACCTGGTGGCCATCACCTCTGCACTT
S G F T G N D L V A I T S A L

AATACATTAGCCAGCTATGGATATAATCTCAACACTTTAGGTTTA
N T L A S Y G Y N L N T L G L

Figure 7E

```
GGTCTCAGTCAAGCAGCAGCAACAGGGGCTTTGGCTGCAGCAGCT
 G   L   S   Q   A   A   A   T   G   A   L   A   A   A   A

GCCAGTGCCCAACCCAGCAGCAGCCAATTTATTGGCCACC
 A   S   A   N   P   A   A   A   A   A   N   L   L   A   T

TATGCCAGTGAAGCCTCAGCTGGCAGCACAGCTGGTGGTACG
 Y   A   S   E   A   S   A   S   G   S   T   A   G   G   T

GCGGGGACATTTGCATTAGGTAGCCTGGCTGCTACTGCTGCA
 A   G   T   F   A   L   G   S   L   A   A   T   A   A

ACCAATGGATATTTTGGAGCTGCTTCTCCCTAGCTGCCAGTGCC
 T   N   G   Y   F   G   A   A   S   P   L   A   A   S   A
```

Figure 7F

Hom #3

```
ATTCTAGGAACAGAAAAGTCCACAGATGGATCCAAGGATGTAGTT
 I  L  G  T  E  K  S  T  D  G  S  K  D  V

GAAATAGCAGTGCCAGAAAACTTAGTTGGTGCAATACTTGGCAAA
 E  I  A  V  P  E  N  L  V  G  A  I  L  G  K

GGAGGGAAAACATTAGTGGAATACCAGGAGTTGACTGGTGCAAGG
 G  G  K  T  L  V  E  Y  Q  E  L  T  G  A  R

ATACAGATCTCCAAAAAGGAGAATTCGTACCTGGCACAAGGAAT
 I  Q  I  S  K  K  G  E  F  V  P  G  T  R  N
                    1500

CGGAAGGTAACCATTACTGGAACCAGCTGCAACACAGGCTGCT
 R  K  V  T  I  T  G  T  P  A  A  T  Q  A  A

CAATATTTAATTACACAAGGATCACATATGAGCAAGGAGTTCGG
 Q  Y  L  I  T  Q  R  I  T  Y  E  Q  G  V  R

GCTGCCAATCCTCAGAAAGTGGGTTGAGTGCCCC
 A  A  N  P  Q  K  V  G  *
```

Figure 7G

AGTTACACATCAGATTGTTTTAACCCCTCCTTACCCCATTT
TCAAGAAGGATGTACTGTACTTTGCAGAAGTGAAGTTTTCT
GTTATTAATATATAATATGCAAATGAATGCGACTATGTTGA
CAATGTGTATATGTAAATAATATGTGTTTTACCAGATGTTTC
ATAGAAAGAAATTTTTCTTGATCTGTTTTGTTCTCTATACTT
TGCTTGTGTATATTTGTCAGAGGTGTTTCTAGTGTAAGATTT
AAGCCCTGCCATTTTACCAGCATTATTGTAGTTTAATGATTGA
ATGTAG

ACAGGGATATGCGTATAGTTTTCAGTATTAGTTCTAGATAAC
ACTAAATTAACTACTGTTAGGTTGAGTATGGTGGGTCAGTG
ACCTAAAATGGAGTGAGGCCAAAGCACTGTCCTGTAAGTCTT
ACTTCCTGCTTAGGGCACAGTGAAGTAGGAAACAATATTTTG
AAAATAAGTTTTAAATTTAAAATGATCAAAAAGCAATATAGT
TGCATAAAAGCACTGTAAAATATTTAAAGGTTAAAACTGTG
GAAAATTATATTGGTAAGTTTACAGATCAATAAAAGCACCTG
TTCTCCATCTGAACTAGACAATGGAAATAATGCTGCATGCTG
CCATGCCCATTCTTCATCATTTGTAAGTTCAACAAAAGTTC
TCACATGGAGTCCCACCTCTTCAGAGGTTGCACATTTGTTTT
TAAGACTGAATTCACTACTGATCCCATCGCCCTGGCCGAGACA
GTCATTACTCCATTAACATCCTACTGTTAGACACATAA

Figure 7H

CTGTGGTACAGGATTGGAAATTATAAACAAAAGTGAAGTGCC
AACAAATTATTGATAGCTGATAATGTTTCATATCTGCAACTG
CTTGATAAGTATGTTGCATTTTAAGAGCTATAATTGTGTATA
ATTTGTTAACACTAGAAACCTATTAGTATTGTGAATGTAGAT
TTTACTGTGAAGCTATCTGTGATTAGCTGTTGCTCCCATG
ATGGAGTCTTTGCAGCATGGCGCTAGCAGCCAATGCAGTTTC
TATACTCGGTAATTGCATGTTTGTGGAGCATTTTATGTC
ACCAACCAGACAGTATTCCTGCATGCTTATTAGAAGAGGC
AGCTTATCTTGAGAGGTAGTGTTATCTACCTTTGTCAGGCTT
TTTGACAGGTCATTTCAGAGTAAGCCTTTGTTCCCAAGACCC
AACAACTGTCACCCCTCTCTGTACCTCTCCTGAGTGCCAACT
GTCCAGGCCATTTGACACACCATCTGTTAACCTCTGAG

TTTGCCCACTCAAGGCCACTCATAGGGGCATCCTAGCCCCTGTG
CACTCAGCACTCATAGGATCATCCAGACTCTCATGCGGCATGC
AGTCTAATCATGACAAATAAATGCTGCTACTCTGATATCTGGCT
GAGCAACTGAATTACAAAAGAGAATTACTTCCATCTCAACTTC
AACCCATTGATTACGTCCATCCTAGCAAGCTAAATGGCATCCC
AGCTGCTCCTTGTCTGTGCAACCAATTAAAGAACAATGAGTGTG
ATGCTCCATGTCTGAATTTCGTCCAGCCCTCTCTGAACTGTG
ATCTTTGTCCTCATGAACTTTCCCTTTGTTCATTGAACTATA
TGGACTCTTCATTTCATATTGATTACTGTGCAATTACTTTT
GGACATTGAGAACTTGAAATTATTGGAATTC

Figure 8

```
Hom #1  L . . K V L I P . . . S Y A A G S I I G K G G Q T I V Q L Q K E T G A T I K L S K
Hom #2  V - - K I - - V P - - N - - - - - - - G - - - A T V K A V M E Q S G A W V Q L S Q
Hom #3  V - - E I A V P E N L V G A I L G - - - G K T L V E Y Q E L T G A R I Q I S K
SIV     V Y P L P P N - T F G L I L G R S S N Y K K G L Q I Y P G V I D N D Y T
MMTV    V K G T L P E G T T G L I I G R S S N Y K K G L E V L P G V I D S D F Q
```

Homology 1 & 2:   41% Identity
Homology 1 & 3:   43% Identity
Homology 2 & 3:   57% Identity Homology 2 & SIV:      54% Homology;  35% Identity
Homology & MMTV:  ~40% Homology;  30% Identity

RI FUSION ANTIGEN RECOGNIZED BY ANTIBODIES ASSOCIATED WITH PARANEOPLASTIC OPSOCLONUS AND METHODS OF USE THEREOF

This is a continuation of application U.S. Ser. No. 07/691,559, filed Apr. 25, 1991 now abandoned.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

Paraneoplastic neurologic syndromes are disorders in which patients with malignancy develop neurologic dysfunction which is not a result of a tumor mass or metastasis (1,2). It has been suggested that these tumors express neuronal antigens, which elicit an immune response which are appropriate to the tumor, but destructive to the nervous system (3). One such syndrome which has been recently characterized is paraneoplastic opsoclonus (PO), in which brainstem dysfunction develops in patients with underlying malignancies resulting in a characteristic disorder of eye movement. In adults, the most common associated malignancies are breast cancer (4) or lung cancer (5).

SUMMARY OF THE INVENTION

An isolated nucleic acid sequence encoding Ri paraneoplastic antigenic polypeptide is provided by this invention. This invention also provides a purified Ri antigenic polypeptide and compositions containing the purified Ri antigenic polypeptide. The invention additionally provides a method of producing a polypeptide having the biological activity of Ri antigenic polypeptide.

A method of detecting an antibody associated with paraneoplastic opsoclonus (PO) is provided by this invention. This method comprises contacting a suitable sample with a purified Ri antigenic polypeptide labelled with a detectable marker under suitable conditions so as to form a complex between the purified Ri antigenic polypeptide and the antibody, detecting the presence of any complex so formed, thereby detecting an antibody associated with paraneoplastic opsoclonus.

Also provided by this invention is a method of determining whether a patient exhibiting neurological symptoms harbors a tumor expressing Ri antigen, which comprises contacting a suitable tumor sample from the patient, with an antibody directed against Ri antigen, the antibody being labeled with a detectable marker, under suitable conditions so as to form a complex between the antibody and the tumor antigen, detecting the presence of any complex so formed, the presence of complex being a positive determination that the patient has a tumor which expresses Ri antigenic polypeptide.

A method of inhibiting the proliferation of neoplastic cells in a patient having paraneoplastic opsoclonus also is provided by this invention. This method comprises administering to the patient an effective amount of an antibody directed to the Ri paraneoplastic tumor antigen, the antibody being labeled with a therapeutic agent, in an amount which is effective to inhibit the proliferation of the neoplastic cells, thereby inhibiting the proliferation of neoplastic cells in a patient exhibiting paraneoplastic opsoclonus.

This invention further provides a method of imaging neoplastic cells in a patient, wherein the neoplastic cells are associated with paraneoplastic opsoclonus, which comprises administering to the patient an effective amount of an antibody directed to Ri paraneoplastic opsoclonus antigen, the antibody being labelled with an imaging agent, under suitable conditions to form a detectable complex between the antibody and the Ri antigen, imaging any complex so formed, thereby imaging neoplastic cells in a patient.

BRIEF DESCRIPTION OF THE FIGURES

FIGS. 5A–5E shows the amino acid sequence of the pRi8 plasmid. The sequence of this DNA was determined in multiple sequence runs on both strands. Also shown is the amino acid sequence of the Ri fusion protein.

FIGS. 7A–7H shows the nucleotide sequence and predicted amino acid sequence of the Ri gene.

FIG. 8 shows the percent homology between the Ri consensus sequences, the simian ! immunodeficiency virus (SIV) and the mouse mammary tumor virus (MMTV).

DETAILED DESCRIPTION OF THE INVENTION

Figure 1:
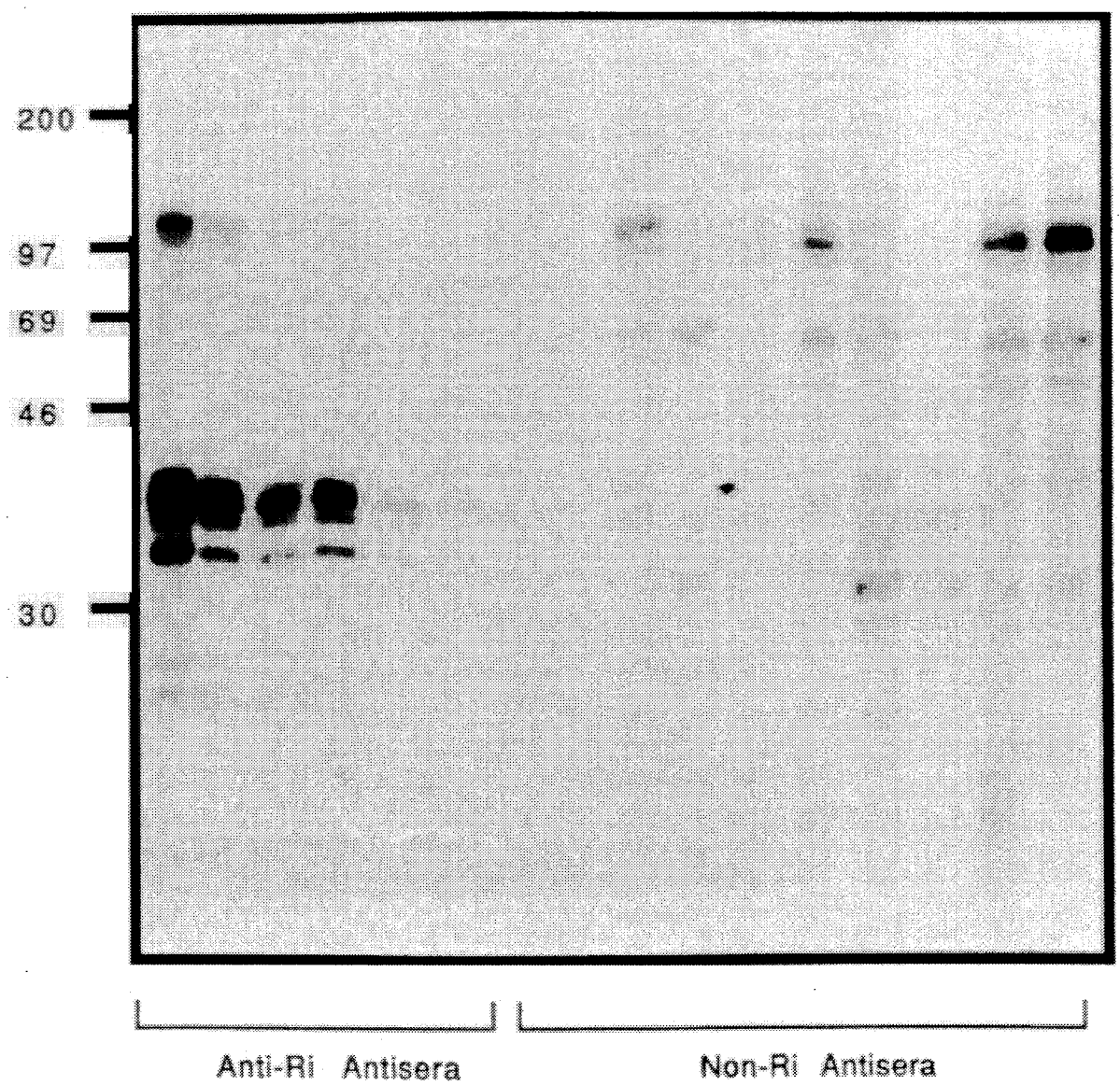
FIG. 1 shows a Western blot of the cloned Ri8 fusion protein probed with anti-Ri antiserum. A fusion protein of $M_r 40$ kDa is recognized by anti-Ri antiserum (FIG. 1, "Anti-Ri Antisera": lanes titrations of antiserum from one patient), but not by normal human serum (FIG. 1, "Non-Ri Antisera": sera from 9 different patients are shown).

This invention provides an isolated nucleic acid sequence encoding an Ri paraneoplastic opsoclonus antigenic polypeptide. As used herein, the term Ri paraneoplastic opsoclonus antigenic polypeptide encompasses any amino acid sequence having the biological activity of an Ri antigenic protein, i.e., a protein which may specifically form a complex with an antibody which is characteristic of paraneoplastic opsoclonus. This antibody has also been called autoantibody ("anti-Ri"). An autoantibody (anti-Ri) has recently been described in 8 patients with PO and breast cancer that recognizes both a neuronal nuclear antigen(s) of $M_r$50 and 75 kDa (3,4), as well as tumor cells in sections of breast cancer obtained from three of these patients. This antibody, i.e., anti-Ri, is characteristically found in patients with paraneoplastic opsoclonus, a disorder of the brain found most commonly in association with neoplasms of the breast, lung and neuroblastoma.

In one embodiment of this invention, the isolated nucleic acid sequence described hereinabove is DNA. In other embodiments of this invention, the isolated nucleic acid sequence described hereinabove is cDNA, or is RNA. In the preferred embodiment of this invention, the isolated nucleic acid sequence is the same or substantially the same as the sequence as shown in sequence FIG. 5.

An isolated nucleic acid sequence described hereinabove operatively linked to a promoter of RNA transcription is also provided by this invention. A vector which comprises the isolated nucleic acid molecule described hereinabove is further provided. Suitable vectors comprise, but are not limited to, a plasmid or a virus. This vector may be transfected into a suitable host cell to form a host vector system for the production of a polypeptide having the biological activity of the Ri antigenic polypeptide.

The following plasmid designated pRi8, was deposited on Apr. 25, 1991 with the American Type culture Collection in Rockville, Md. U.S.A. 20852, under ATCC Accession No. 75006. This deposit was made pursuant to the provisions of the Budapest Treaty on the International Recognition of the Deposit of Microorganisms for the Purposes of Patent Procedure (Budapest Treaty).

This invention further provides an isolated DNA or cDNA molecule described hereinabove wherein the host cell is selected from the group consisting of bacteria cells such as *E. coli*, yeast and fungi cells, insect cells and animal cells. Suitable animal cells include, but are not limited to Vero cells, HeLa cells, Cos cells, CV1 cells and primary mouse cells.

Further provided by this invention is a method for producing a polypeptide having the biological activity of the Ri antigenic polypeptide comprising the steps of: a) culturing the host vector system described hereinabove under suitable conditions permitting production of the polypeptide and b) recovering the polypeptide produced. This invention also provides the polypeptide produced by this method.

Throughout this application, references to specific nucleotides are to nucleotides present on the coding strand of the nucleic acid. The following standard abbreviations are used throughout the specification to indicate specific nucleotides:

C=cytosine

A=adenosine

T=thymidine

G=guanosine

U=uracil

This invention also encompasses DNAs and cDNAs which encode amino acid sequences which differ from those of the Ri paraneoplastic antigenic polypeptide, but which should not produce phenotypic changes. Alternatively, this invention also encompasses DNAs and cDNAs which hybridize to the DNA and cDNA of the subject invention. Hybridization methods are well known to those of ordinary skill in the art. This invention also encompasses cDNA and DNA molecules characterized by changes in non-coding regions that do not alter the phenotype of the polypeptide produced.

Also provided by this invention is a purified, Ri antigenic polypeptide. The purified Ri antigenic polypeptide may be labeled with a detectable marker. For the purposes of this invention, suitable detectable markers include, but are not limited to detectable markers selected from the group consisting of radioisotopes, dyes, enzymes and biotin.

This invention further provides an antibody directed to an epitope on the Ri antigenic polypeptide. In one embodiment of this invention, the antibody is a monoclonal antibody e.g., a mouse monoclonal antibody. In another embodiment of this invention, the antibody is a human monoclonal antibody. Another embodiment of the invention the antibody is a polyclonal antibody.

For the isolation of mouse monoclonal antibodies, eight week old mice may be injected interperitoneally with about 50 micrograms of a synthetic, purified Ri antigenic polypeptide, (prepared as described above) in complete Freud's adjuvant 1:1 volume. Mice will then be boosted, at monthly intervals, with the polypeptide, mixed with incomplete Freund's adjuvant, and bled through the tail vein. On days 4, 3, and 2 prior to fusion, mice will be boosted intravenously with 50 micrograms of the polypeptide in saline. Splenocytes will then be fused with non-secreting myeloma cells according to procedures which have been described and are known to those of ordinary skill in the art to which this invention pertains. Some time later, approximately two weeks later, hybridoma supernatant will then be screened for binding activity against the Ri antigenic polypeptide as described hereinafter.

Positive clones will then be isolated and propagated. Isolates of human monoclonal antibodies will be similar except β cells will be isolated from patients and transformed with EBV. β cells will then be fused with non-secreting myeloma cells according to procedures which have been described and are known to those of ordinary skill in the art to which this invention pertains. Some time later, approximately two weeks later, hybridoma supernatant will then be screened for binding activity against the Ri antigenic polypeptide as described hereinafter. Positive clones will then De isolated and propagated.

In addition, this invention also provides the antibody, e.g., monoclonal antibody described hereinabove conjugated to a therapeutic agent. For the purposes of this invention, suitable therapeutic agents include, but are not limited to, a therapeutic agent selected from the group consisting of radioisotopes, toxins, toxoids, and chemotherapeutic agents. Also provided by this invention is the monoclonal antibody described hereinabove conjugated to a detectable marker. Suitable detectable markers include, but are not limited to, enzymes, radioisotopes, dyes and biotin. This invention further provides monoclonal antibodies as described hereinabove conjugated to an imaging agent. Suitable imaging agents include, but are not limited to radioisotopes, such as, $^{32}P$, $^{35}S$, and $^{131}I$. Methods of utilizing the monoclonal antibody conjugated to an imaging agent, to image tumor cells, are well known to those of ordinary skill in the art.

Also provided by this invention are pharmaceutical compositions comprising the purified Ri antigenic polypeptide described hereinabove alone, or conjugated to any one of the following, a detectable marker, a therapeutic agent, or an imaging agent, as described hereinabove and a pharmaceutically acceptable carrier. Further provided are pharmaceutical compositions comprising the antibody or monoclonal antibody described hereinabove alone, or conjugated to any one of the following, a detectable marker, a therapeutic agent, or an imaging agent. As used herein, the term "pharmaceutically acceptable carrier" encompasses any of the standard pharmaceutical carriers, such as phosphate buffered saline solution, water, emulsions, such as a oil/water emulsions, and various types of wetting agents.

A method of detecting an antibody associated with paraneoplastic opsoclonus "PO", is also provided by this invention. This method comprises contacting a suitable sample with a purified Ri antigenic polypeptide described hereinabove under conditions so as to form a complex between the purified Ri antigenic polypeptide and the antibody, detecting the presence of any complex so formed, thereby detecting an antibody associated with paraneoplastic opsoclonus. Suitable samples include any sample suspected to contain an antibody associated with paraneoplastic opsoclonus such as serum, cerebral-spinal fluid or a tissue sample. In one embodiment of the invention the synthetic, purified Ri antigenic polypeptide is labeled with a detectable marker selected from the group consisting of radioisotopes, dyes, enzymes and biotin. For the purposes of this invention, suitable radioisotopes include, but are not limited to, $^{32}P$, $^{35}S$, and $^{131}I$.

Also provided by this invention is a method of determining whether a patient exhibiting neurological symptoms harbors a tumor expressing the Ri antigen, which comprises obtaining a suitable tumor sample from the patient, contacting the suitable tumor sample with a monoclonal antibody directed against the Ri antigen, under suitable conditions so as to form a complex between the antibody and the Ri antigen, detecting the presence of any complex so formed, the presence of a complex being a positive determination that the patient harbors a tumor expressing the Ri antigenic polypeptide. In one embodiment of this invention, the monoclonal antibody is labeled with a detectable marker. For the purposes of this invention, suitable detectable markers include, but are not limited to a detectable marker selected from the group consisting of radioisotopes, dyes, enzymes and biotin. Suitable radioisotopes have been described hereinabove.

Further provided by this invention is a method of inhibiting the proliferation of neoplastic cells in a patient exhibiting paraneoplastic opsoclonus syndrome. This method comprises administering to the patient an effective amount of the antibody or composition described hereinabove conjugated to a therapeutic agent, in an amount which is effective to inhibit the proliferation of the neoplastic cells, and under suitable conditions so as to form a complex between an antigen associated with the neoplasm and the monoclonal antibody, thereby inhibiting the proliferation of the neoplastic cells. As used herein, an effective amount is any amount which is effective to inhibit the proliferation of neoplastic cells. As is known to those of ordinary skill in the art, effective amounts vary with the type of therapeutic agent utilized, as well the neoplastic cell tumor being treated. It is well known to those of ordinary skill in the art how to determine an effective amount of a suitable therapeutic agent.

As used herein, "administering" means a method of administering to the patient. Such methods are well known to those skilled in the art and include, but are not limited to administration orally, intravenously, or parenterally. Administration of the agent may be effected continuously or intermittently, such that the amount of the therapeutic agent in the patient is effective to inhibit proliferation of neoplastic cells. For the purposes of this invention suitable therapeutic agents include radioisotopes, toxins, toxoids, and chemotherapeutic agents.

Also provided by this invention is a method of imaging neoplastic cells in a patient, wherein the neoplastic cells are associated with paraneoplastic opsoclonus. The method comprises administering to the patient the monoclonal antibody described hereinabove which is labelled with an imaging agent, for example $^{131}I$, or a composition containing the same. The antibody is administered in an amount and under such conditions so as to allow the Ri antigen present on or within the neoplastic cells to form a complex between the antibody and the antigen. Any complex so formed, is then detected, allowing the imaging of neoplastic cells in a patient having neoplastic cells expressing Ri antigen. As is well known to those of ordinary skill in the art, a suitable amount of monoclonal antibody or composition is any amount which is effective to image the neoplastic cells, for example, from about 0.1 mCi to about 50.0 Mci. In addition, an effective amount of the monoclonal antibody may be an amount from about 0.01 mg to about 100 mg. Suitable methods of administering the imaging agent are as described hereinabove.

Imaging of any complex so formed may be carried out using single photon computed emission tomography (SPECT) or by using a gamma camera.

This invention provides a method to isolate and clone specific anti-tumor antigen human antibodies. The β lymphocytes will be isolated from patient's blood, transformed with E.B.V. (Epstein Barr Virus) and selected by the specific recognition of the recombinant Ri antigen.

Further provided by this invention is a diagnostic method useful for predicting the presence of tumors in patients. This method comprises contacting a suitable sample, such as serum from the patient with a labelled antigenic polypeptide of this invention under suitable conditions so as to form a complex between the antigenic polypeptide and any antibody in the sample, detecting the presence of any complex so formed, the presence of complex being predictive of the presence of a tumor. For example such tumors may include small cell lung or breast cancer, or neuroblastoma.

This invention is illustrated in the Experimental Detail section which follow. These sections are set forth to aid in an understanding of the invention but are not intended to, and should not be construed to, limit in any way the invention as set forth in the claims which follow thereafter.

MATERIALS AND METHODS

Screening of λ Expression Libraries

Recombinant phage were screened at a density of $10^5$ pfu per 150 mm plate of *E. coli* XLI-Blue. After incubation for 6 hours at 37° C., the plates were overlaid with filters soaked in IPTG (10 mM) and incubated for a further 12 hours at 37° C. The filters were then removed and incubated with anti-Ri sera (at 1:500 dilution) for 2 hours at room temperature. Filters were washed in TBST (50 mM Tris pH7.5, 100 mM NaCl, 0.2% TRITON™) and incubated with $^{125I}$ protein A. After washing with TBST, filters were exposed to XAR5™ film at −70° C. Clones yielding positive signals were purified by several rounds of antibody screening until 100% of the plaques gave positive signals.

Analysis of Fusion Proteins

Phage clones were subcloned into the pBluescript (pBS) vector using the Phage rescue protocol. Individual clones were grown to an OD of 0.6 and induced by adding IPTG. Cell lysates were prepared in 2% SDS, and resolved by 8% polyacrylamide SDS gel electrophoresis and transferred to nitrocellulose. Filters were blocked in 5% milk in PBS, incubated with antisera, washed incubated with $I^{125}$ protein A, and exposed as described above.

DNA Sequence Analysis

All sequencing was based on the dideoxy termination method. Double strand DNA was sequenced on both strands using a variety of vector based and internal oligonucleotide primers. Sequence analysis was facilitated by the use of the MACVECTOR™ sequence analysis program (IBI).

RESULTS

Cloning of the Ri Gene

Antiserum from a single patient with PO was used to screen a cerebellar cDNA expression vector library. Initial screening of $8 \times 10^5$ plaques yielded three positive clones. One, λRi8, was chosen for further evaluation. Phagemid was excised from λRi8 using the helper phage R408, and the resulting plasmid, termed pRi8, cloned and propagated in *E coli* host XL1-blue.

FIG. 1 shows a Western blot of the cloned Ri8 fusion protein probed with anti-Ri antiserum. A fusion protein of $M_r$40 kDa is recognized by anti-Ri antiserum (FIG. 1, "Anti-Ri Antisera": lanes titrations of antiserum from one patient), but not by normal human serum (FIG. 1, "Non-Ri Antisera": sera from 9 different patients are shown). These results demonstrate that serum from a patient affected with paraneoplastic opsoclonus recognizes an antigenic epitope encoded by the cDNA of the recombinant clone pRi8.

To confirm the identity of the Ri8 clone as the antigen recognized by PO antiserum, λRi8 fusion protein was used to affinity purify antibody from anti-Ri antiserum. Nitrocellulose filters were blotted from plates confluent with either λRi8 or, as a negative control, an irrelevant lambda clone, and incubated with native anti-Ri antiserum. After washing the filters extensively, specifically bound ("affinity purified") antibody was eluted at low pH and used to probe Western blots.

Figure 2:
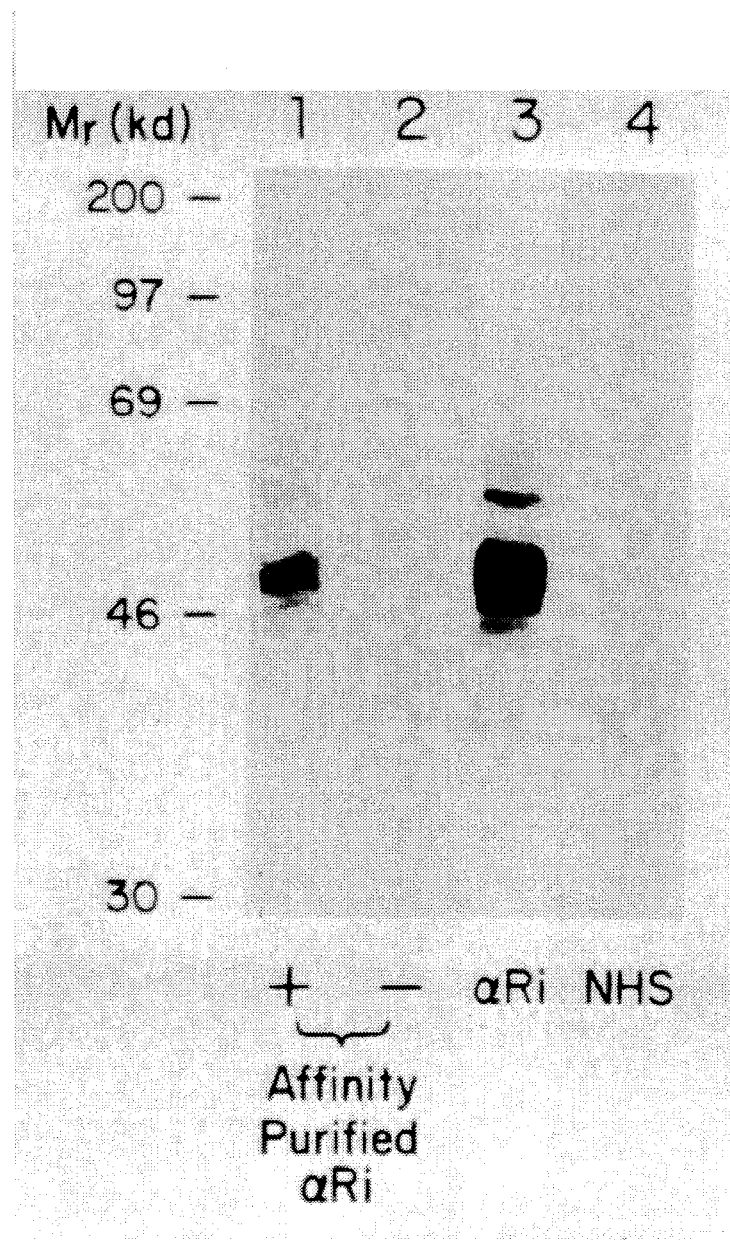
FIG. 2 shows a Western blot of human Purkinje cell neuronal extracts. Native anti-Ri antiserum binds to a major antigen of 50 kDa and a minor antigen of higher Mr (as previously described, see reference 4) (lane 3); normal human serum gives no signal (lane 4). AntiRi antiserum affinity purified with the λRi8 fusion protein bound antigens of identical $M_r$ to those recognized by native anti-Ri antiserum (lane 1 versus lane 3); anti-Ri antiserum mock affinity purified with an irrelevant lambda clone showed no detectable binding to Purkinje proteins (lane 2).

FIG. 2 shows a Western blot of human Purkinje cell neuronal extracts. Native anti-Ri antiserum binds to a major antigen of 50 kDa and a minor antigen of higher $M_r$ (as previously described, (see reference 4); FIG. 2, lane 3); normal human serum gives no signal (FIG. 2, lane 4). AntiRi antiserum affinity purified with the λRi8 fusion protein bound antigens of identical $M_r$ to those recognized by native anti-Ri antiserum (FIG. 2, lane 1 versus lane 3); anti-Ri antiserum mock affinity purified with an irrelevant lambda clone showed no detectable binding to Purkinje proteins (FIG. 2, lane 2). These results demonstrate that the cloned Ri fusion protein encodes an antigenic epitope that 1) is recognized by Ri antiserum, and 2) is related to the Ri neuronal antigen.

To determine whether the affinity purified anti-Ri antisera recognized tumor cell antigens, additional Western blots were performed. Both a small cell lung cancer and neuroblastoma tumor cell line expressed antigens recognized by native anti-Ri antisera of approximately the same $M_r$ as those recognized in Purkinje cell neurons; anti-Ri antiserum affinity purified with cloned Ri fusion protein recognized antigens identical in $M_r$ to those recognized by native anti-Ri antiserum. These results demonstrate that the cloned Ri fusion protein encodes an antigenic epitope that is present in small cell lung cancer and neuroblastoma cell lines.

Figure 3:
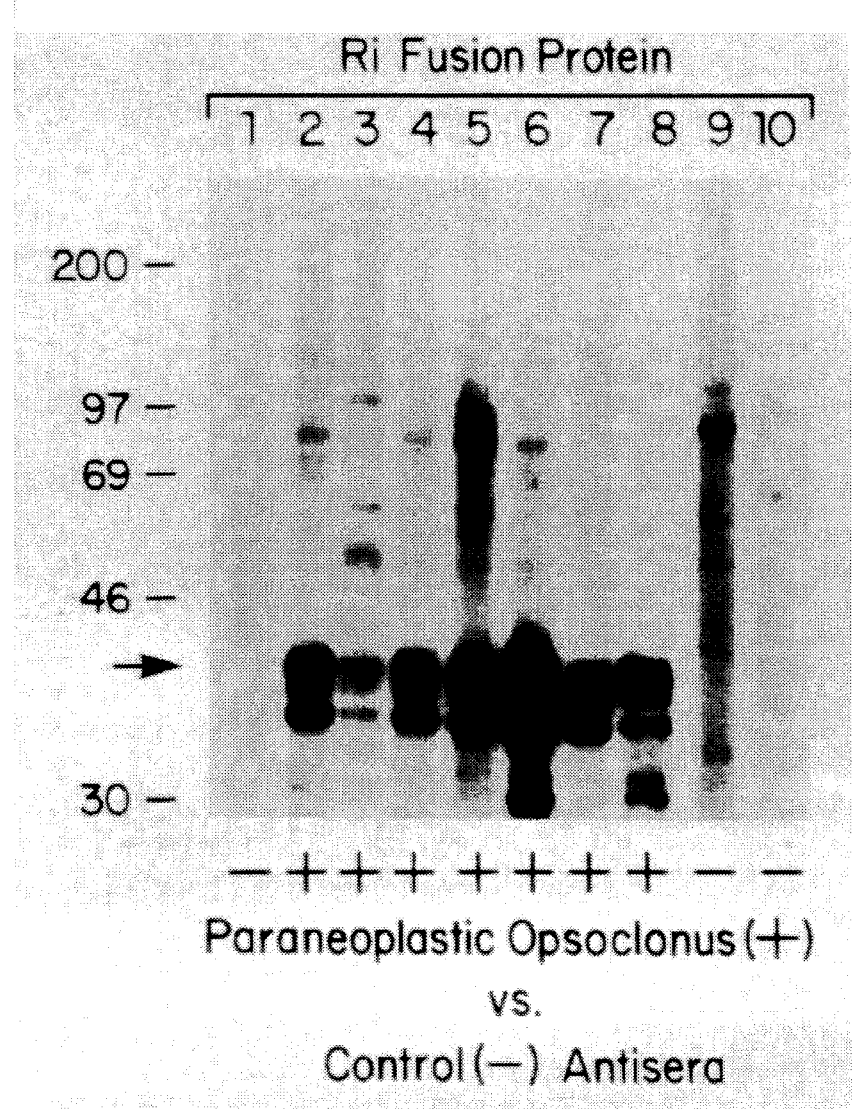
FIG. 3 shows a Western blot of pRi8 fusion protein incubated with various antisera: those labelled "+" are from patients with PO and breast cancer, and those labelled "–" are from normal sera. In each case, sera from patients with paraneoplastic opsoclonus showed significant immunoreactivity with the Ri fusion protein (band identified by arrow in FIG. 4).

TO extend these observations, Ri8 fusion protein was probed with antisera or CSF from 7 different patients known to have the PO syndrome (as reported in reference 4). FIG. 3 shows a Western blot of pRi8 fusion protein incubated with various antisera. Those labelled "+" are from patients with PO and breast cancer, and those labelled "−" are from normal sera. In each case, sera from patients with PO showed significant immunoreactivity with the Ri fusion protein (band identified by arrow in FIG. 4). In no case did the control antisera show immunoreactivity with the Ri fusion protein, although at high titre some showed non-specific immunoreactivity against an *E. coli* antigen of high $M_r$ (approximately 90–105 kDa, FIG. 3). Antisera from one additional patient with PO has subsequently been demonstrated to show comparable immunoreactivity against the Ri fusion protein, while antisera from an additional 20 normal sera or non-Ri paraneoplastic sera have been demonstrated to show no immunoreactivity against the Ri fusion protein.

Characterization of the Ri Gene

Figure 4:
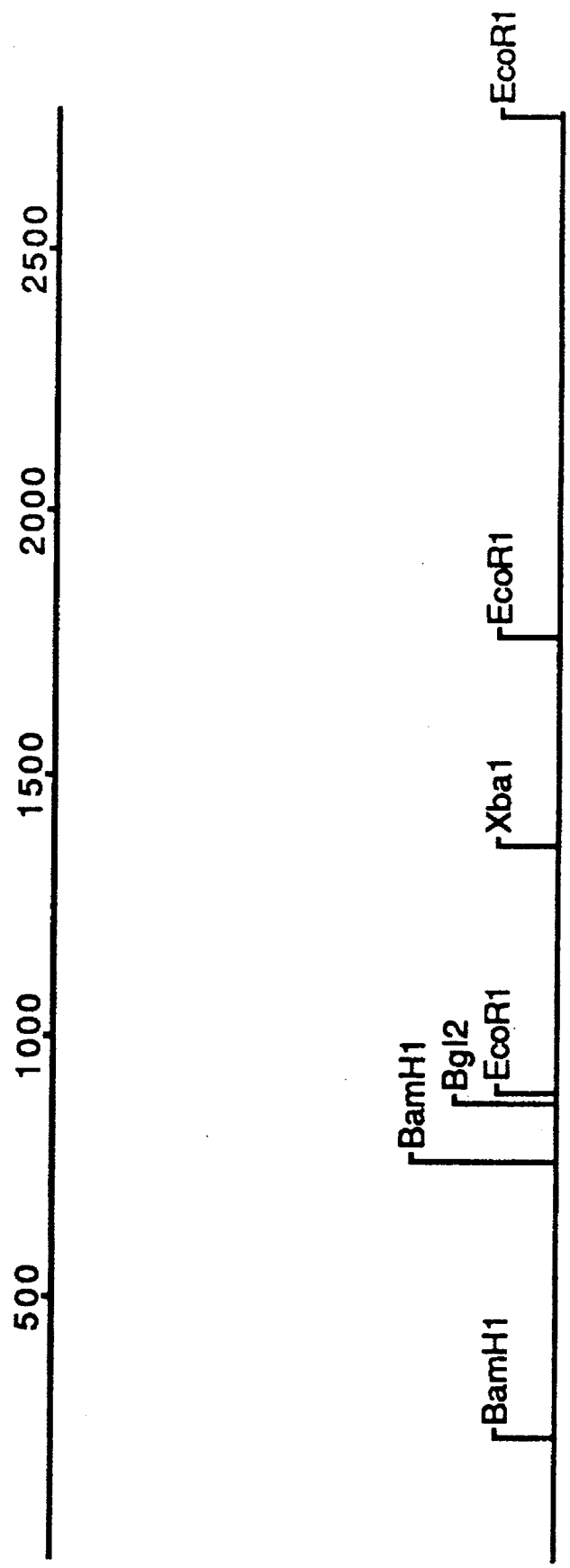
FIG. 4 shows a restriction map of the pRi8 plasmid; the approximate size of the cloned insert is 2.7 kb, and it is cleaved by EcoRI twice and BamHI twice to yield a characteristic restriction digest pattern.

Restriction endonuclease digests were performed to determine the orientation, size, and structure of the cDNA present in plasmid pRi8. FIG. 4 shows a restriction map of the pRi8 plasmid; the approximate size of the cloned insert is 2.7 kb, and it is cleaved by EcoR1 twice and BamH1 twice to yield a characteristic restriction digest pattern. The dideoxy method was used to determine the DNA sequence of the entire pRi8 plasmid (FIGS. 5A–5E). An open reading frame extending from one end of the clone approximately 340 amino acids was identified. The sequence of this DNA was determined in multiple sequence runs on both strands, and is shown in FIGS. 5A–5E. Also shown in FIG. 5 is the predicted amino acid sequence of the Ri fusion protein.

Figure 6:
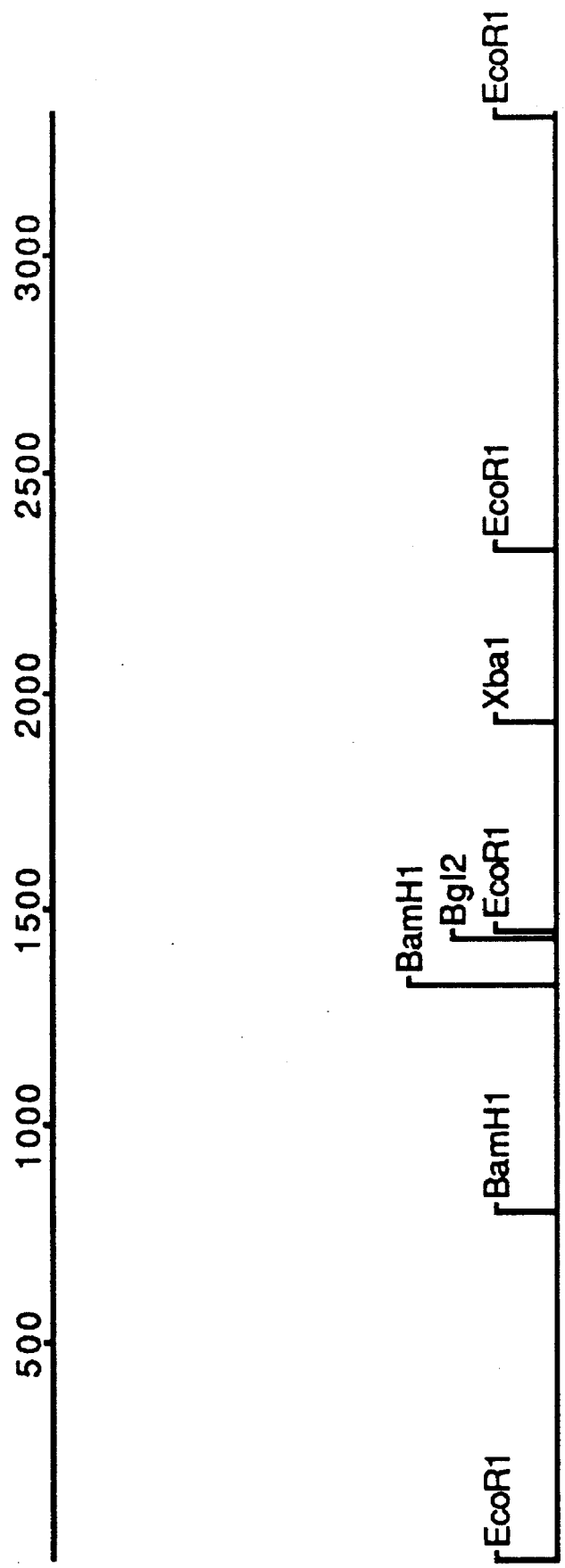
FIG. 6 shows a restriction map of the consensus Ri gene. A number of overlapping clones which were identified which allowed a consensus sequence of the Ri gene to be obtained, identical to pRi8, but including an additional 600 nucleotides.

Additional clones representing the full Ri gene were obtained by nucleic acid hybridization. A PCR probe was generated from oligonucleotides at the 5' end of pRi8, gel purified and used to screen λgt11 libraries generated from different areas of the brain. A number of overlapping clones were identified which allowed a consensus sequence of the Ri gene to be obtained, identical to pRi8, but including an additional 600 nucleotides. The restriction map of the consensus Ri gene is shown in FIG. 6, and the nucleotide sequence and amino acid sequence of this gene are shown in FIGS. 7A–7H. The open reading frame at the 5' term to the Ri protein extends to the 5' end of the consensus Ri gene sequence (FIGS. 7A–7H), the predicted peptide encoded by this gene is 55 kDa, approximately the size of the protein detected on Western blot (see FIG. 2). Furthermore, there are two methionine residues (amino acid 20 and 21) at the 5' terminus that could potentially act as N-terminal amino acids of the Ri gene.

The nucleic acid and protein sequence of the Ri gene were analyzed for homology with known sequences deposited in the DNA database at Los Alamos (Genbank and GenPept). No sequence was found to share significant homology with the Ri gene. Thus it was concluded that the Ri gene encodes a novel gene and encodes a novel peptide. When sequence analysis was performed on the Ri gene looking for internal homologies, a striking conservation of sequence, at both the nucleic acid and protein level, was observed in a 111 bp, 37 amino acid stretch of sequence. This motif was repeated three times throughout the sequence of the Ri gene, and is shown both in FIG. 7A–7H (boxed out sequences, indicated also by "Hom #N"), and, in detail, in FIG. 8. Amino acid identities are indicated by a vertical bar or "Λ" conservative amino acid changes suggesting homology are indicated by a ":". The 3 homologous motifs ranged from 41 to 57% identity at the amino acid level. Searching this subsequence for homologies in the DNA database revealed significant homology with a segment of the pol gene of the retroviridae. The percent homology between the Ri consensus sequences, the simian immunodeficiency virus (SIV) and the mouse mammary tumor virus (MMTV) is shown in FIG. 8.

Different Ri Gene Transcripts Identified in Different Areas of the Brain

Figure 9:
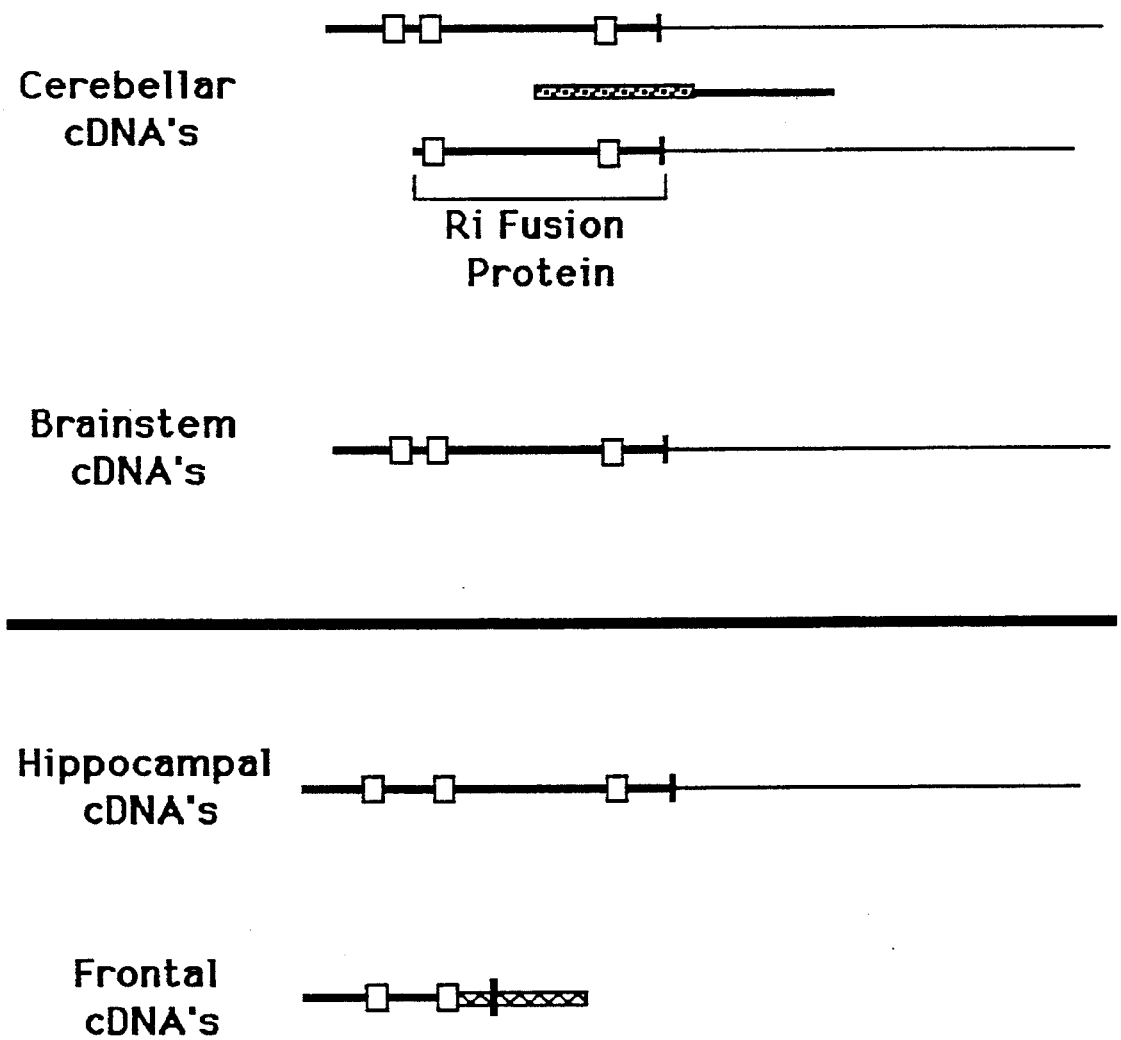
FIG. 9 compares the Ri consensus gene sequence with the sequences derived from clones isolated from various areas of the brain.

In the process of generating the sequence of the Ri gene, a number of additional clones were found that overlapped, in part, but not in their entirety, the Ri consensus gene sequence; these are illustrated schematically in FIG. 9. In the cerebellum, FIG. 9 illustrates the consensus of Ri gene sequence (top line); three open boxes illustrate the location of the three homologous sequences identified, and the dark bar represents the open reading frame encoding the predicted Ri protein. The Ri fusion protein encoding clone, pRi8, is also illustrated. In addition, a third clone is illustrated, which is homologous with Ri sequences just distal to the stop codon of the Ri gene, and has additional, novel, sequences 5' of this homology.

In the brainstem, clones were identified that were identical to the cerebellar consensus Ri gene sequence. In the hippocampus and frontal cortex, however, a novel sequence was found to be inserted into the Ri gene in between homology sequences one and two (see FIG. 9). This relatively short insertion, of 72 bp, is exactly in reading frame with the Ri gene, and encodes a peptide insertion of 24 amino acids. These data suggest that this sequence represents an alternatively spliced exon, present in Ri mRNA transcripts of the hippocampus and frontal cortex, but not the brainstem or cerebellum. Further, they imply a modified, longer form of the Ri protein may be expressed in some areas of the brain.

Finally, an additional form of the Ri gene was identified in a clone from the frontal cortex (see FIG. 9). This clone is identical to the Ri consensus sequence, includes the exon sequence referred to above, but terminates Ri identity exactly following the end of homology sequence 2. Distal sequence of this clone shows a termination codon after only 8 amino acids of divergent sequence. This suggests that a truncated form of the Ri protein may be expressed in the frontal cortex.

Discussion

The data presented demonstrate that a cDNA clone, pRi8, has been isolated that encodes a protein, termed Ri, that is recognized by patients with paraneoplastic opsoclonus. Further cloning has extended the available sequence of this gene to predict the sequence of a 550 amino acid peptide, roughly equal the full length of the Ri. major antigen.

Nucleic acid sequencing has determined that the Ri gene is novel, compared with known gene sequences in the available DNA databanks. Furthermore, an internally homologous sequence is identified that shares some homology with the retroviridea. The specific sequence shared, in 6 retrovirus sequences identified, is with a protease like gene within the pol domain of the retrovirus genome. However, the sequence homology is not with the identified protease domain consensus sequence; thus whether this homology gives an immediate clue to the function of the Ri protein, or simply identifies what is likely to be an important functional domain, is unclear.

A number of alternatively spliced forms of the Ri gene have been identified in different areas of the brain. This may prove to be of interest regarding the role of the Ri antigen in the pathogenesis of paraneoplastic opsoclonus. It has been reported and confirmed that antisera from Ri patients recognizes an antigen present in the nuclei of all neurons, yet the neurologic syndrome of paraneoplastic opsoclonus is a specific one, perhaps involving only the brainstem and cerebellum. Of interest, one form of the Ri protein was found common to both of these areas of the brain (the form missing an exon sequence of 72 bp, see FIG. 9). It is possible that specific variants of the Ri protein may be found to more closely resemble the form of the Ri antigen expressed in tumor cells, and thus account, at least in part, for the specificity seen clinically between underlying malignancy and neurologic disorder present in paraneoplastic opsoclonus.

REFERENCES

1. Hall, T. C., editor (1974): Paraneoplastic Syndromes. Annals of the New York Academy of Science, Vol. 230. New York.
2. Shnider, B. I., and Manalo, A. (1979): Paraneoplastic syndromes: unusual manifestations of malignant disease. Dis. Mon. 25:1–60.
3. Posner, J. B. and Furneaux, H. M. (1990): Paraneoplastic Syndromes. In: Immunologic Mechanisms in Neurologic and Psychiatric Disease, ed B. H. Waksman, Raven Press, Ltd., New York.
4. Luque, F. A. et al. (1991). Anti-Ri: an antibody associated with paraneoplastic opsoclonus and breast cancer. Ann Neurol 29:241–251.
5. Digre, K. B. (1986): opsoclonus in adults. Arch. Neurol., 43:1165–1175.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

5,614,371

-continued ( A ) LENGTH: 2756 base pairs
( B ) TYPE: nucleic acid
( C ) STRANDEDNESS: double
( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
( A ) NAME/KEY: CDS
( B ) LOCATION: 1..1029
( D ) OTHER INFORMATION:

( x i ) SEQUENCE DESCRIPTION: SEQ ID NO:1:

| CCA | GAT | GAT | CCA | GAT | CGC | ATC | AAA | CAA | GTA | AAG | ATT | ATA | GTT | CCC | AAC | 48 |
| Pro | Asp | Asp | Pro | Asp | Arg | Ile | Lys | Gln | Val | Lys | Ile | Ile | Val | Pro | Asn | |
| 1 | | | | 5 | | | | | 10 | | | | | 15 | | |

| AGC | ACA | GCA | GGT | CTG | ATA | ATA | GGG | AAG | GGA | GGT | GCT | ACT | GTG | AAG | GCT | 96 |
| Ser | Thr | Ala | Gly | Leu | Ile | Ile | Gly | Lys | Gly | Gly | Ala | Thr | Val | Lys | Ala | |
| | | | 20 | | | | | 25 | | | | | 30 | | | |

| GTA | ATG | GAG | CAG | TCA | GGG | GCT | TGG | GTG | CAG | CTT | TCC | CAG | AAA | CCT | GAT | 144 |
| Val | Met | Glu | Gln | Ser | Gly | Ala | Trp | Val | Gln | Leu | Ser | Gln | Lys | Pro | Asp | |
| | | 35 | | | | | 40 | | | | | 45 | | | | |

| GGG | ATC | AAC | TTG | CAA | GAG | AGG | GTT | GTC | ACT | GTG | AGT | GGA | GAA | CCT | GAA | 192 |
| Gly | Ile | Asn | Leu | Gln | Glu | Arg | Val | Val | Thr | Val | Ser | Gly | Glu | Pro | Glu | |
| | 50 | | | | | 55 | | | | | 60 | | | | | |

| CAA | AAC | CGA | AAA | GCT | GTT | GAA | CTT | ATC | ATC | CAG | AAG | ATA | CAA | GAG | GAT | 240 |
| Gln | Asn | Arg | Lys | Ala | Val | Glu | Leu | Ile | Ile | Gln | Lys | Ile | Gln | Glu | Asp | |
| 65 | | | | | 70 | | | | | 75 | | | | | 80 | |

| CCA | CAA | AGT | GGC | AGC | TGT | CTC | AAT | ATC | AGT | TAT | GCC | AAT | GTG | ACA | GGT | 288 |
| Pro | Gln | Ser | Gly | Ser | Cys | Leu | Asn | Ile | Ser | Tyr | Ala | Asn | Val | Thr | Gly | |
| | | | | 85 | | | | | 90 | | | | | 95 | | |

| CCA | GTG | GCA | AAT | TCC | AAT | CCA | ACC | GGA | TCT | CCT | TAT | GCA | AAC | ACT | GCT | 336 |
| Pro | Val | Ala | Asn | Ser | Asn | Pro | Thr | Gly | Ser | Pro | Tyr | Ala | Asn | Thr | Ala | |
| | | | 100 | | | | | 105 | | | | | 110 | | | |

| GAA | GTG | TTA | CCA | ACT | GCT | GCA | GCA | GCT | GCA | GGG | CTA | TTA | GGA | CAT | GCT | 384 |
| Glu | Val | Leu | Pro | Thr | Ala | Ala | Ala | Ala | Ala | Gly | Leu | Leu | Gly | His | Ala | |
| | | 115 | | | | | 120 | | | | | 125 | | | | |

| AAC | CTT | GCT | GGC | GTT | GCA | GCC | TTT | CCA | GCA | GTT | TTA | TCT | GGC | TTC | ACA | 432 |
| Asn | Leu | Ala | Gly | Val | Ala | Ala | Phe | Pro | Ala | Val | Leu | Ser | Gly | Phe | Thr | |
| | 130 | | | | | 135 | | | | | 140 | | | | | |

| GGC | AAT | GAC | CTG | GTG | GCC | ATC | ACC | TCT | GCA | CTT | AAT | ACA | TTA | GCC | AGC | 480 |
| Gly | Asn | Asp | Leu | Val | Ala | Ile | Thr | Ser | Ala | Leu | Asn | Thr | Leu | Ala | Ser | |
| 145 | | | | | 150 | | | | | 155 | | | | | 160 | |

| TAT | GGA | TAT | AAT | CTC | AAC | ACT | TTA | GGT | TTA | GGT | CTC | AGT | CAA | GCA | GCA | 528 |
| Tyr | Gly | Tyr | Asn | Leu | Asn | Thr | Leu | Gly | Leu | Gly | Leu | Ser | Gln | Ala | Ala | |
| | | | | 165 | | | | | 170 | | | | | 175 | | |

| GCA | ACA | GGG | GCT | TTG | GCT | GCA | GCT | GCC | AGT | GCC | AAC | CCA | GCA | GCA | | 576 |
| Ala | Thr | Gly | Ala | Leu | Ala | Ala | Ala | Ala | Ser | Ala | Asn | Pro | Ala | Ala | | |
| | | | 180 | | | | | 185 | | | | | 190 | | | |

| GCA | GCA | GCC | AAT | TTA | TTG | GCC | ACC | TAT | GCC | AGT | GAA | GCC | TCA | GCC | AGT | 624 |
| Ala | Ala | Ala | Asn | Leu | Leu | Ala | Thr | Tyr | Ala | Ser | Glu | Ala | Ser | Ala | Ser | |
| | | 195 | | | | | 200 | | | | | 205 | | | | |

| GGC | AGC | ACA | GCT | GGT | GGT | ACG | GCG | GGG | ACA | TTT | GCA | TTA | GGT | AGC | CTG | 672 |
| Gly | Ser | Thr | Ala | Gly | Gly | Thr | Ala | Gly | Thr | Phe | Ala | Leu | Gly | Ser | Leu | |
| | 210 | | | | | 215 | | | | | 220 | | | | | |

| GCT | GCT | GCT | ACT | GCT | GCA | ACC | AAT | GGA | TAT | TTT | GGA | GCT | GCT | TCT | CCC | 720 |
| Ala | Ala | Ala | Thr | Ala | Ala | Thr | Asn | Gly | Tyr | Phe | Gly | Ala | Ala | Ser | Pro | |
| 225 | | | | | 230 | | | | | 235 | | | | | 240 | |

| CTA | GCT | GCC | AGT | GCC | ATT | CTA | GGA | ACA | GAA | AAG | TCC | ACA | GAT | GGA | TCC | 768 |
| Leu | Ala | Ala | Ser | Ala | Ile | Leu | Gly | Thr | Glu | Lys | Ser | Thr | Asp | Gly | Ser | |

```
                    245                        250                        255
AAG  GAT  GTA  GTT  GAA  ATA  GCA  GTG  CCA  GAA  AAC  TTA  GTT  GGT  GCA  ATA        816
Lys  Asp  Val  Val  Glu  Ile  Ala  Val  Pro  Glu  Asn  Leu  Val  Gly  Ala  Ile
                    260                        265                   270

CTT  GGC  AAA  GGA  GGG  AAA  ACA  TTA  GTG  GAA  TAC  CAG  GAG  TTG  ACT  GGT        864
Leu  Gly  Lys  Gly  Gly  Lys  Thr  Leu  Val  Glu  Tyr  Gln  Glu  Leu  Thr  Gly
               275                        280                   285

GCA  AGG  ATA  CAG  ATC  TCC  AAA  AAA  GGA  GAA  TTC  GTA  CCT  GGC  ACA  AGG        912
Ala  Arg  Ile  Gln  Ile  Ser  Lys  Lys  Gly  Glu  Phe  Val  Pro  Gly  Thr  Arg
          290                        295                   300

AAT  CGG  AAG  GTA  ACC  ATT  ACT  GGA  ACA  CCA  GCT  GCA  ACA  CAG  GCT  GCT        960
Asn  Arg  Lys  Val  Thr  Ile  Thr  Gly  Thr  Pro  Ala  Ala  Thr  Gln  Ala  Ala
305                      310                  315                        320

CAA  TAT  TTA  ATT  ACA  CAA  AGG  ATC  ACA  TAT  GAG  CAA  GGA  GTT  CGG  GCT       1008
Gln  Tyr  Leu  Ile  Thr  Gln  Arg  Ile  Thr  Tyr  Glu  Gln  Gly  Val  Arg  Ala
                    325                      330                   335

GCC  AAT  CCT  CAG  AAA  GTG  GGT  TGAGTGCCCC AGTTACACAT CAGATTGTTT                   1059
Ala  Asn  Pro  Gln  Lys  Val  Gly
               340

TAACCCCTCC TTTACCCCAT TTTCAAGAAG GATGTACTGT ACTTTGCAGA AGTGAAGTTT                     1119
TTCTGTTATT AATATATAAT TATGCAAATG AATGCGACTA TGTTGACAAT GTGTATATGT                     1179
AAATAATATG TGTTTTACCA GATGTTTCAT AGAAAGAATT TTTTCTTGAT CTGTTTTGTT                     1239
CTCTATACTT TGCTTGTGTA TATTTGTCAG AGGTGTTTCT AGTGTAAGAT TTAAGCCTGC                     1299
CATTTTACCA GCATTATTGT AGTTTAATGA TTGAATGTAG ACAGGGATAT GCGTATAGTT                     1359
TTCAGTATTA GTTCTAGATA ACACTAAATT AACTACTGTT AGGTTGAGTA TGGTGGGGTC                     1419
AGTGACCTAA AATGGAGTGA GGCCAAAGCA CTGTCCTGTA AGTCTTACTT CCTGCTTAGG                     1479
GCACAGTGAA GTAGGAAACA ATATTTTGAA AATAAGTTTT AAATTTAAAA TGATCAAAAA                     1539
GCAATATAGT TGCATAAAAG CACTGTAAAA TATTTAAAAG GTTAAAACTG TGGAAAATTA                     1599
TATTGGTAAG TTTACAGATC AATAAAAGCA CCTGTTCTCC ATCTGAACTA GACAATGGAA                     1659
ATAATGCTGC ATGCTGCCAT GGCCCATTCT TCATCATTTG TAAGTTCAAC AAAAGTTCTC                     1719
ACATGGAGTC CCACCTCTTC AGAGGTTGCA CATTTGTTTT TAAGACTGAA TTCACTACTG                     1779
ATCCCATCGC CTGGCCGAGA CAGTCATTAC TCCATTAACA TCCTACTGTT AGACACATAA                     1839
CTGTGGTACA GGATTGGAAA TTATAAACAA AAGTGAAGTG CCAACAAATT ATTGATAGCT                     1899
GATAATGTTT CATATCTGCA ACTGCTTGAT AAGTATGTTG CATTTAAGA GCTATAATTG                      1959
TGTATAATTT GTTAACACTA GAAACCTATT AGTATTGTGA ATGTAGATTT TACTGTGAAG                     2019
CTATCTGTGA TTTAGCTGTT TGCTCCCATG ATGGAGTCTT TGCAGCATGG CGCTAGCAGC                     2079
CAATGCAGTT TCTATACTCG GTAATTTGCA TGTTTTGTGG AGCATTTTA TGTCACCAAC                      2139
CAGACAGTAT TTCCTGCATG CTTATTTAGA AGAGGCAGCT TATCTTGAGA GGTAGTGTTA                     2199
TCTACCTTTG TCAGGCTTTT TGACAGGTCA TTTCAGAGTA AGCCTTTGTT CCCAAGACCC                     2259
AACAACTGTC ACCCTCTTCT GTACCTCTCC TGAGTGCCAA CTGTCCAGGC CATTTGACAC                     2319
ACCATCTGTT AACCTCTGAG TTTGCCCACT CAAGGCCACT CATAGGGGCA TCCTAGCCCT                     2379
GTGCACTCAG CACTCATAGG ATCATCCAGA CTCTCATGCG GCATGCAGTC TAATCATGAC                     2439
AAATAATGCT GCTACTCTGA TATCTGGCTG AGCAACTGAA TTACAAAGA GAATTACTTC                      2499
CATCTCAACT TCAACCCATT GATTACGTCC ATCCTAGCAA GCTAAATGGC ATCCCAGCTG                     2559
CTCCTTTCTG TGCAACCAAT TAAAGAACAA TGAGTGTGAT GCTCCATGTC TGAATTTCGT                     2619
CCAGCCTCTC TCTGAACTGT GATCTTTGTC CTCATGAACT TTCCCTTTTG TTCATTGAAC                     2679
```

```
TATATGGACT CTTCATTTCA TATTGATTAC TGTGCAATTT ACTTTTGGAC ATTGAGAACT    2739

TGAAATTATT GGAATTC                                                   2756
```

( 2 ) INFORMATION FOR SEQ ID NO:2:

( i ) SEQUENCE CHARACTERISTICS:
        ( A ) LENGTH: 343 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro  Asp  Asp  Pro  Asp  Arg  Ile  Lys  Gln  Val  Lys  Ile  Ile  Val  Pro  Asn
 1              5                        10                       15

Ser  Thr  Ala  Gly  Leu  Ile  Ile  Gly  Lys  Gly  Gly  Ala  Thr  Val  Lys  Ala
          20                       25                       30

Val  Met  Glu  Gln  Ser  Gly  Ala  Trp  Val  Gln  Leu  Ser  Gln  Lys  Pro  Asp
          35                       40                       45

Gly  Ile  Asn  Leu  Gln  Glu  Arg  Val  Val  Thr  Val  Ser  Gly  Glu  Pro  Glu
          50                       55                       60

Gln  Asn  Arg  Lys  Ala  Val  Glu  Leu  Ile  Ile  Gln  Lys  Ile  Gln  Glu  Asp
 65                      70                       75                       80

Pro  Gln  Ser  Gly  Ser  Cys  Leu  Asn  Ile  Ser  Tyr  Ala  Asn  Val  Thr  Gly
                    85                       90                       95

Pro  Val  Ala  Asn  Ser  Asn  Pro  Thr  Gly  Ser  Pro  Tyr  Ala  Asn  Thr  Ala
               100                      105                      110

Glu  Val  Leu  Pro  Thr  Ala  Ala  Ala  Ala  Gly  Leu  Leu  Gly  His  Ala
               115                      120                      125

Asn  Leu  Ala  Gly  Val  Ala  Ala  Phe  Pro  Ala  Val  Leu  Ser  Gly  Phe  Thr
          130                      135                      140

Gly  Asn  Asp  Leu  Val  Ala  Ile  Thr  Ser  Ala  Leu  Asn  Thr  Leu  Ala  Ser
145                      150                      155                     160

Tyr  Gly  Tyr  Asn  Leu  Asn  Thr  Leu  Gly  Leu  Gly  Leu  Ser  Gln  Ala  Ala
                    165                      170                      175

Ala  Thr  Gly  Ala  Leu  Ala  Ala  Ala  Ala  Ala  Ser  Ala  Asn  Pro  Ala  Ala
               180                      185                      190

Ala  Ala  Ala  Asn  Leu  Leu  Ala  Thr  Tyr  Ala  Ser  Glu  Ala  Ser  Ala  Ser
          195                      200                      205

Gly  Ser  Thr  Ala  Gly  Gly  Thr  Ala  Gly  Thr  Phe  Ala  Leu  Gly  Ser  Leu
     210                      215                      220

Ala  Ala  Ala  Thr  Ala  Ala  Thr  Asn  Gly  Tyr  Phe  Gly  Ala  Ala  Ser  Pro
225                      230                      235                     240

Leu  Ala  Ala  Ser  Ala  Ile  Leu  Gly  Thr  Glu  Lys  Ser  Thr  Asp  Gly  Ser
                    245                      250                      255

Lys  Asp  Val  Val  Glu  Ile  Ala  Val  Pro  Glu  Asn  Leu  Val  Gly  Ala  Ile
               260                      265                      270

Leu  Gly  Lys  Gly  Gly  Lys  Thr  Leu  Val  Glu  Tyr  Gln  Glu  Leu  Thr  Gly
          275                      280                      285

Ala  Arg  Ile  Gln  Ile  Ser  Lys  Lys  Gly  Glu  Phe  Val  Pro  Gly  Thr  Arg
     290                      295                      300

Asn  Arg  Lys  Val  Thr  Ile  Thr  Gly  Thr  Pro  Ala  Ala  Thr  Gln  Ala  Ala
305                      310                      315                     320

Gln  Tyr  Leu  Ile  Thr  Gln  Arg  Ile  Thr  Tyr  Glu  Gln  Gly  Val  Arg  Ala
                    325                      330                      335

Ala  Asn  Pro  Gln  Lys  Val  Gly
```

340

(2) INFORMATION FOR SEQ ID NO:3:

(i) SEQUENCE CHARACTERISTICS:
        (A) LENGTH: 3318 base pairs
        (B) TYPE: nucleic acid
        (C) STRANDEDNESS: double
        (D) TOPOLOGY: unknown (ii) MOLECULE TYPE: cDNA (iii) HYPOTHETICAL: N (iv) ANTI-SENSE: N (ix) FEATURE:
        (A) NAME/KEY: CDS
        (B) LOCATION: 1..1590
        (D) OTHER INFORMATION:

(xi) SEQUENCE DESCRIPTION: SEQ ID NO:3:

```
GAA  TTC  CGA  CAA  AAC  AAA  AGG  GAG  AAC  CTT  CTC  CCG  GTA  GCA  GCG  GCA      48
Glu  Phe  Arg  Gln  Asn  Lys  Arg  Glu  Asn  Leu  Leu  Pro  Val  Ala  Ala  Ala
 1                   5                        10                       15

GGA  ACT  GCA  AAC  ATG  ATG  GCG  GCA  GCT  CCC  ATC  CAG  CAG  AAC  GGG  ACC      96
Gly  Thr  Ala  Asn  Met  Met  Ala  Ala  Ala  Pro  Ile  Gln  Gln  Asn  Gly  Thr
               20                             25                      30

CAC  ACT  GGG  GTT  CCC  ATA  GAC  CTG  GAC  CCG  CCG  GAC  TCG  CGG  AAA  AGG     144
His  Thr  Gly  Val  Pro  Ile  Asp  Leu  Asp  Pro  Pro  Asp  Ser  Arg  Lys  Arg
          35                        40                       45

CCG  CTG  GAA  GCC  CCC  CCT  GAA  GCC  GGC  AGC  ACC  AAG  AGG  ACC  AAT  ACG     192
Pro  Leu  Glu  Ala  Pro  Pro  Glu  Ala  Gly  Ser  Thr  Lys  Arg  Thr  Asn  Thr
     50                        55                       60

GGC  GAA  GAC  GGC  CAG  TAT  TTT  CTA  AAG  GTT  CTC  ATA  CCT  AGT  TAT  GCT     240
Gly  Glu  Asp  Gly  Gln  Tyr  Phe  Leu  Lys  Val  Leu  Ile  Pro  Ser  Tyr  Ala
65                        70                       75                       80

GCT  GGA  TCT  ATA  ATT  GGG  AAG  GGA  GGA  CAG  ACA  ATT  GTT  CAG  TTG  CAA     288
Ala  Gly  Ser  Ile  Ile  Gly  Lys  Gly  Gly  Gln  Thr  Ile  Val  Gln  Leu  Gln
                    85                       90                       95

AAA  GAA  ACT  GGA  GCC  ACC  ATC  AAG  CTG  TCT  AAG  CTG  TCT  AAG  TCC  AAA     336
Lys  Glu  Thr  Gly  Ala  Thr  Ile  Lys  Leu  Ser  Lys  Leu  Ser  Lys  Ser  Lys
               100                           105                     110

GAT  TTT  TAC  CCA  GGT  ACT  ACT  GAG  CGA  GTG  TGC  TTG  ATC  CAG  GGA  ACG     384
Asp  Phe  Tyr  Pro  Gly  Thr  Thr  Glu  Arg  Val  Cys  Leu  Ile  Gln  Gly  Thr
          115                       120                      125

GTT  GAA  GCA  CTG  AAT  GCA  GTT  CAT  GGA  TTC  ATT  GCA  GAA  AAA  ATT  CGA     432
Val  Glu  Ala  Leu  Asn  Ala  Val  His  Gly  Phe  Ile  Ala  Glu  Lys  Ile  Arg
     130                       135                      140

GAA  ATG  CCC  CAA  AAT  GTG  GCC  AAG  ACA  GAA  CCA  GTC  AGC  ATT  CTA  CAA     480
Glu  Met  Pro  Gln  Asn  Val  Ala  Lys  Thr  Glu  Pro  Val  Ser  Ile  Leu  Gln
145                      150                      155                     160

CCC  CAG  ACC  ACC  GTT  AAT  CCA  GAT  CGC  ATC  AAA  CAA  ACA  TTG  CCA  TCT     528
Pro  Gln  Thr  Thr  Val  Asn  Pro  Asp  Arg  Ile  Lys  Gln  Thr  Leu  Pro  Ser
               165                           170                     175

TCC  CCA  ACT  ACC  ACC  AAG  TCC  TCT  CCA  TCT  GAT  CCC  ATG  ACC  ACC  TCC     576
Ser  Pro  Thr  Thr  Thr  Lys  Ser  Ser  Pro  Ser  Asp  Pro  Met  Thr  Thr  Ser
               180                           185                     190

AGA  GCT  AAT  CAG  GTA  AAG  ATT  ATA  GTT  CCC  AAC  AGC  ACA  GCA  GGT  CTG     624
Arg  Ala  Asn  Gln  Val  Lys  Ile  Ile  Val  Pro  Asn  Ser  Thr  Ala  Gly  Leu
               195                           200                     205

ATA  ATA  GGG  AAG  GGA  GGT  GCT  ACT  GTG  AAG  GCT  GTA  ATG  GAG  CAG  TCA     672
Ile  Ile  Gly  Lys  Gly  Gly  Ala  Thr  Val  Lys  Ala  Val  Met  Glu  Gln  Ser
     210                       215                      220
```

| | | | | | | | | | | | | | | | | |
|---|---|---|---|---|---|---|---|---|---|---|---|---|---|---|---|---|
| GGG | GCT | TGG | GTG | CAG | CTT | TCC | CAG | AAA | CCT | GAT | GGG | ATC | AAC | TTG | CAA | 720 |
| Gly | Ala | Trp | Val | Gln | Leu | Ser | Gln | Lys | Pro | Asp | Gly | Ile | Asn | Leu | Gln | |
| 225 | | | | 230 | | | | | 235 | | | | | | 240 | |
| GAG | AGG | GTT | GTC | ACT | GTG | AGT | GGA | GAA | CCT | GAA | CAA | AAC | CGA | AAA | GCT | 768 |
| Glu | Arg | Val | Val | Thr | Val | Ser | Gly | Glu | Pro | Glu | Gln | Asn | Arg | Lys | Ala | |
| | | | | 245 | | | | | 250 | | | | | 255 | | |
| GTT | GAA | CTT | ATC | ATC | CAG | AAG | ATA | CAA | GAG | GAT | CCA | CAA | AGT | GGC | AGC | 816 |
| Val | Glu | Leu | Ile | Ile | Gln | Lys | Ile | Gln | Glu | Asp | Pro | Gln | Ser | Gly | Ser | |
| | | | 260 | | | | | 265 | | | | | 270 | | | |
| TGT | CTC | AAT | ATC | AGT | TAT | GCC | AAT | GTG | ACA | GGT | CCA | GTG | GCA | AAT | TCC | 864 |
| Cys | Leu | Asn | Ile | Ser | Tyr | Ala | Asn | Val | Thr | Gly | Pro | Val | Ala | Asn | Ser | |
| | | 275 | | | | | 280 | | | | | 285 | | | | |
| AAT | CCA | ACC | GGA | TCT | CCT | TAT | GCA | AAC | ACT | GCT | GAA | GTG | TTA | CCA | ACT | 912 |
| Asn | Pro | Thr | Gly | Ser | Pro | Tyr | Ala | Asn | Thr | Ala | Glu | Val | Leu | Pro | Thr | |
| | 290 | | | | | 295 | | | | | 300 | | | | | |
| GCT | GCA | GCA | GCT | GCA | GGG | CTA | TTA | GGA | CAT | GCT | AAC | CTT | GCT | GGC | GTT | 960 |
| Ala | Ala | Ala | Ala | Ala | Gly | Leu | Leu | Gly | His | Ala | Asn | Leu | Ala | Gly | Val | |
| 305 | | | | | 310 | | | | | 315 | | | | | 320 | |
| GCA | GCC | TTT | CCA | GCA | GTT | TTA | TCT | GGC | TTC | ACA | GGC | AAT | GAC | CTG | GTG | 1008 |
| Ala | Ala | Phe | Pro | Ala | Val | Leu | Ser | Gly | Phe | Thr | Gly | Asn | Asp | Leu | Val | |
| | | | | 325 | | | | | 330 | | | | | 335 | | |
| GCC | ATC | ACC | TCT | GCA | CTT | AAT | ACA | TTA | GCC | AGC | TAT | GGA | TAT | AAT | CTC | 1056 |
| Ala | Ile | Thr | Ser | Ala | Leu | Asn | Thr | Leu | Ala | Ser | Tyr | Gly | Tyr | Asn | Leu | |
| | | | 340 | | | | | 345 | | | | | 350 | | | |
| AAC | ACT | TTA | GGT | TTA | GGT | CTC | AGT | CAA | GCA | GCA | GCA | ACA | GGG | GCT | TTG | 1104 |
| Asn | Thr | Leu | Gly | Leu | Gly | Leu | Ser | Gln | Ala | Ala | Ala | Thr | Gly | Ala | Leu | |
| | | 355 | | | | | 360 | | | | | 365 | | | | |
| GCT | GCA | GCA | GCT | GCC | AGT | GCC | AAC | CCA | GCA | GCA | GCA | GCA | GCC | AAT | TTA | 1152 |
| Ala | Ala | Ala | Ala | Ser | Ala | Asn | Pro | Ala | Ala | Ala | Ala | Ala | Asn | Leu | | |
| | 370 | | | | | 375 | | | | | 380 | | | | | |
| TTG | GCC | ACC | TAT | GCC | AGT | GAA | GCC | TCA | GCC | AGT | GGC | AGC | ACA | GCT | GGT | 1200 |
| Leu | Ala | Thr | Tyr | Ala | Ser | Glu | Ala | Ser | Ala | Ser | Gly | Ser | Thr | Ala | Gly | |
| 385 | | | | | 390 | | | | | 395 | | | | | 400 | |
| GGT | ACG | GCG | GGG | ACA | TTT | GCA | TTA | GGT | AGC | CTG | GCT | GCT | GCT | ACT | GCT | 1248 |
| Gly | Thr | Ala | Gly | Thr | Phe | Ala | Leu | Gly | Ser | Leu | Ala | Ala | Ala | Thr | Ala | |
| | | | | 405 | | | | | 410 | | | | | 415 | | |
| GCA | ACC | AAT | GGA | TAT | TTT | GGA | GCT | GCT | TCT | CCC | CTA | GCT | GCC | AGT | GCC | 1296 |
| Ala | Thr | Asn | Gly | Tyr | Phe | Gly | Ala | Ala | Ser | Pro | Leu | Ala | Ala | Ser | Ala | |
| | | | 420 | | | | | 425 | | | | | 430 | | | |
| ATT | CTA | GGA | ACA | GAA | AAG | TCC | ACA | GAT | GGA | TCC | AAG | GAT | GTA | GTT | GAA | 1344 |
| Ile | Leu | Gly | Thr | Glu | Lys | Ser | Thr | Asp | Gly | Ser | Lys | Asp | Val | Val | Glu | |
| | | 435 | | | | | 440 | | | | | 445 | | | | |
| ATA | GCA | GTG | CCA | GAA | AAC | TTA | GTT | GGT | GCA | ATA | CTT | GGC | AAA | GGA | GGG | 1392 |
| Ile | Ala | Val | Pro | Glu | Asn | Leu | Val | Gly | Ala | Ile | Leu | Gly | Lys | Gly | Gly | |
| | 450 | | | | | 455 | | | | | 460 | | | | | |
| AAA | ACA | TTA | GTG | GAA | TAC | CAG | GAG | TTG | ACT | GGT | GCA | AGG | ATA | CAG | ATC | 1440 |
| Lys | Thr | Leu | Val | Glu | Tyr | Gln | Glu | Leu | Thr | Gly | Ala | Arg | Ile | Gln | Ile | |
| 465 | | | | | 470 | | | | | 475 | | | | | 480 | |
| TCC | AAA | AAA | GGA | GAA | TTC | GTA | CCT | GGC | ACA | AGG | AAT | CGG | AAG | GTA | ACC | 1488 |
| Ser | Lys | Lys | Gly | Glu | Phe | Val | Pro | Gly | Thr | Arg | Asn | Arg | Lys | Val | Thr | |
| | | | | 485 | | | | | 490 | | | | | 495 | | |
| ATT | ACT | GGA | ACA | CCA | GCT | GCA | ACA | CAG | GCT | GCT | CAA | TAT | TTA | ATT | ACA | 1536 |
| Ile | Thr | Gly | Thr | Pro | Ala | Ala | Thr | Gln | Ala | Ala | Gln | Tyr | Leu | Ile | Thr | |
| | | | 500 | | | | | 505 | | | | | 510 | | | |
| CAA | AGG | ATC | ACA | TAT | GAG | CAA | GGA | GTT | CGG | GCT | GCC | AAT | CCT | CAG | AAA | 1584 |
| Gln | Arg | Ile | Thr | Tyr | Glu | Gln | Gly | Val | Arg | Ala | Ala | Asn | Pro | Gln | Lys | |
| | | 515 | | | | | 520 | | | | | 525 | | | | |
| GTG | GGT | TGAGTGCCCC | AGTTACACAT | CAGATTGTTT | TAACCCCTCC | TTTACCCCAT | | | | | | | | | | 1640 |
| Val | Gly | | | | | | | | | | | | | | | |
| | 530 | | | | | | | | | | | | | | | |

| | | | | | |
|---|---|---|---|---|---|
| TTTCAAGAAG | GATGTACTGT | ACTTTGCAGA | AGTGAAGTTT | TCTGTTATT | AATATATAAT | 1700 |
| TATGCAAATG | AATGCGACTA | TGTTGACAAT | GTGTATATGT | AAATAATATG | TGTTTACCA | 1760 |
| GATGTTTCAT | AGAAAGAATT | TTTTCTTGAT | CTGTTTTGTT | CTCTATACTT | TGCTTGTGTA | 1820 |
| TATTTGTCAG | AGGTGTTTCT | AGTGTAAGAT | TTAAGCCTGC | CATTTTACCA | GCATTATTGT | 1880 |
| AGTTTAATGA | TTGAATGTAG | ACAGGGATAT | GCGTATAGTT | TTCAGTATTA | GTTCTAGATA | 1940 |
| ACACTAAATT | AACTACTGTT | AGGTTGAGTA | TGGTGGGGTC | AGTGACCTAA | AATGGAGTGA | 2000 |
| GGCCAAAGCA | CTGTCCTGTA | AGTCTTACTT | CCTGCTTAGG | GCACAGTGAA | GTAGGAAACA | 2060 |
| ATATTTTGAA | AATAAGTTTT | AAATTTAAAA | TGATCAAAAA | GCAATATAGT | TGCATAAAAG | 2120 |
| CACTGTAAAA | TATTTAAAAG | GTTAAAACTG | TGGAAAATTA | TATTGGTAAG | TTTACAGATC | 2180 |
| AATAAAAGCA | CCTGTTCTCC | ATCTGAACTA | GACAATGGAA | ATAATGCTGC | ATGCTGCCAT | 2240 |
| GGCCCATTCT | TCATCATTTG | TAAGTTCAAC | AAAAGTTCTC | ACATGGAGTC | CCACCTCTTC | 2300 |
| AGAGGTTGCA | CATTTGTTTT | TAAGACTGAA | TTCACTACTG | ATCCCATCGC | CTGGCCGAGA | 2360 |
| CAGTCATTAC | TCCATTAACA | TCCTACTGTT | AGACACATAA | CTGTGGTACA | GGATTGGAAA | 2420 |
| TTATAAACAA | AAGTGAAGTG | CCAACAAATT | ATTGATAGCT | GATAATGTTT | CATATCTGCA | 2480 |
| ACTGCTTGAT | AAGTATGTTG | CATTTTAAGA | GCTATAATTG | TGTATAATTT | GTTAACACTA | 2540 |
| GAAACCTATT | AGTATTGTGA | ATGTAGATTT | TACTGTGAAG | CTATCTGTGA | TTTAGCTGTT | 2600 |
| TGCTCCCATG | ATGGAGTCTT | TGCAGCATGG | CGCTAGCAGC | CAATGCAGTT | TCTATACTCG | 2660 |
| GTAATTTGCA | TGTTTTGTGG | AGCATTTTTA | TGTCACCAAC | CAGACAGTAT | TTCCTGCATG | 2720 |
| CTTATTTAGA | AGAGGCAGCT | TATCTTGAGA | GGTAGTGTTA | TCTACCTTTG | TCAGGCTTTT | 2780 |
| TGACAGGTCA | TTTCAGAGTA | AGCCTTTGTT | CCCAAGACCC | AACAACTGTC | ACCCTCTTCT | 2840 |
| GTACCTCTCC | TGAGTGCCAA | CTGTCCAGGC | CATTTGACAC | ACCATCTGTT | AACCTCTGAG | 2900 |
| TTTGCCCACT | CAAGGCCACT | CATAGGGGCA | TCCTAGCCCT | GTGCACTCAG | CACTCATAGG | 2960 |
| ATCATCCAGA | CTCTCATGCG | GCATGCAGTC | TAATCATGAC | AAATAATGCT | GCTACTCTGA | 3020 |
| TATCTGGCTG | AGCAACTGAA | TTACAAAAGA | GAATTACTTC | CATCTCAACT | TCAACCCATT | 3080 |
| GATTACGTCC | ATCCTAGCAA | GCTAAATGGC | ATCCCAGCTG | CTCCTTTCTG | TGCAACCAAT | 3140 |
| TAAAGAACAA | TGAGTGTGAT | GCTCCATGTC | TGAATTTCGT | CCAGCCTCTC | TCTGAACTGT | 3200 |
| GATCTTTGTC | CTCATGAACT | TTCCCTTTTG | TTCATTGAAC | TATATGGACT | CTTCATTTCA | 3260 |
| TATTGATTTA | CTGTGCAATT | TACTTTTGGA | CATTGAGAAC | TTGAAATTAT | TGGAATTC | 3318 |

( 2 ) INFORMATION FOR SEQ ID NO:4:

( i ) SEQUENCE CHARACTERISTICS:
        ( A ) LENGTH: 530 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Phe  Arg  Gln  Asn  Lys  Arg  Glu  Asn  Leu  Leu  Pro  Val  Ala  Ala  Ala
 1                 5                  10                  15

Gly  Thr  Ala  Asn  Met  Met  Ala  Ala  Ala  Pro  Ile  Gln  Gln  Asn  Gly  Thr
            20                  25                  30

His  Thr  Gly  Val  Pro  Ile  Asp  Leu  Asp  Pro  Pro  Asp  Ser  Arg  Lys  Arg
        35                  40                  45

Pro  Leu  Glu  Ala  Pro  Pro  Glu  Ala  Gly  Ser  Thr  Lys  Arg  Thr  Asn  Thr
    50                  55                  60
```

-continued

| | | | | | | | | | | | | | | |
|---|---|---|---|---|---|---|---|---|---|---|---|---|---|---|
| Gly | Glu | Asp | Gly | Gln | Tyr | Phe | Leu | Lys | Val | Leu | Ile | Pro | Ser | Tyr | Ala |
| 65 | | | | 70 | | | | | 75 | | | | | 80 |
| Ala | Gly | Ser | Ile | Ile | Gly | Lys | Gly | Gly | Gln | Thr | Ile | Val | Gln | Leu | Gln |
| | | | | 85 | | | | | 90 | | | | | 95 | |
| Lys | Glu | Thr | Gly | Ala | Thr | Ile | Lys | Leu | Ser | Lys | Leu | Ser | Lys | Ser | Lys |
| | | | 100 | | | | | 105 | | | | | 110 | | |
| Asp | Phe | Tyr | Pro | Gly | Thr | Thr | Glu | Arg | Val | Cys | Leu | Ile | Gln | Gly | Thr |
| | | | 115 | | | | | 120 | | | | | 125 | | |
| Val | Glu | Ala | Leu | Asn | Ala | Val | His | Gly | Phe | Ile | Ala | Glu | Lys | Ile | Arg |
| | 130 | | | | | 135 | | | | | 140 | | | | |
| Glu | Met | Pro | Gln | Asn | Val | Ala | Lys | Thr | Glu | Pro | Val | Ser | Ile | Leu | Gln |
| 145 | | | | | 150 | | | | | 155 | | | | | 160 |
| Pro | Gln | Thr | Thr | Val | Asn | Pro | Asp | Arg | Ile | Lys | Gln | Thr | Leu | Pro | Ser |
| | | | | 165 | | | | | 170 | | | | | 175 | |
| Ser | Pro | Thr | Thr | Thr | Lys | Ser | Ser | Pro | Ser | Asp | Pro | Met | Thr | Thr | Ser |
| | | | 180 | | | | | 185 | | | | | 190 | | |
| Arg | Ala | Asn | Gln | Val | Lys | Ile | Ile | Val | Pro | Asn | Ser | Thr | Ala | Gly | Leu |
| | | | 195 | | | | | 200 | | | | | 205 | | |
| Ile | Ile | Gly | Lys | Gly | Gly | Ala | Thr | Val | Lys | Ala | Val | Met | Glu | Gln | Ser |
| | 210 | | | | | 215 | | | | | 220 | | | | |
| Gly | Ala | Trp | Val | Gln | Leu | Ser | Gln | Lys | Pro | Asp | Gly | Ile | Asn | Leu | Gln |
| 225 | | | | | 230 | | | | | 235 | | | | | 240 |
| Glu | Arg | Val | Val | Thr | Val | Ser | Gly | Glu | Pro | Glu | Gln | Asn | Arg | Lys | Ala |
| | | | | 245 | | | | | 250 | | | | | 255 | |
| Val | Glu | Leu | Ile | Ile | Gln | Lys | Ile | Gln | Glu | Asp | Pro | Gln | Ser | Gly | Ser |
| | | | 260 | | | | | 265 | | | | | 270 | | |
| Cys | Leu | Asn | Ile | Ser | Tyr | Ala | Asn | Val | Thr | Gly | Pro | Val | Ala | Asn | Ser |
| | | 275 | | | | | 280 | | | | | 285 | | | |
| Asn | Pro | Thr | Gly | Ser | Pro | Tyr | Ala | Asn | Thr | Ala | Glu | Val | Leu | Pro | Thr |
| | 290 | | | | | 295 | | | | | 300 | | | | |
| Ala | Ala | Ala | Ala | Ala | Gly | Leu | Leu | Gly | His | Ala | Asn | Leu | Ala | Gly | Val |
| 305 | | | | | 310 | | | | | 315 | | | | | 320 |
| Ala | Ala | Phe | Pro | Ala | Val | Leu | Ser | Gly | Phe | Thr | Gly | Asn | Asp | Leu | Val |
| | | | 325 | | | | | 330 | | | | | 335 | | |
| Ala | Ile | Thr | Ser | Ala | Leu | Asn | Thr | Leu | Ala | Ser | Tyr | Gly | Tyr | Asn | Leu |
| | | | 340 | | | | | 345 | | | | | 350 | | |
| Asn | Thr | Leu | Gly | Leu | Gly | Leu | Ser | Gln | Ala | Ala | Ala | Thr | Gly | Ala | Leu |
| | | 355 | | | | | 360 | | | | | 365 | | | |
| Ala | Ala | Ala | Ala | Ala | Ser | Ala | Asn | Pro | Ala | Ala | Ala | Ala | Ala | Asn | Leu |
| | | 370 | | | | | 375 | | | | | 380 | | | |
| Leu | Ala | Thr | Tyr | Ala | Ser | Glu | Ala | Ser | Ala | Ser | Gly | Ser | Thr | Ala | Gly |
| 385 | | | | | 390 | | | | | 395 | | | | | 400 |
| Gly | Thr | Ala | Gly | Thr | Phe | Ala | Leu | Gly | Ser | Leu | Ala | Ala | Ala | Thr | Ala |
| | | | | 405 | | | | | 410 | | | | | 415 | |
| Ala | Thr | Asn | Gly | Tyr | Phe | Gly | Ala | Ala | Ser | Pro | Leu | Ala | Ala | Ser | Ala |
| | | | 420 | | | | | 425 | | | | | 430 | | |
| Ile | Leu | Gly | Thr | Glu | Lys | Ser | Thr | Asp | Gly | Ser | Lys | Asp | Val | Val | Glu |
| | | | 435 | | | | | 440 | | | | | 445 | | |
| Ile | Ala | Val | Pro | Glu | Asn | Leu | Val | Gly | Ala | Ile | Leu | Gly | Lys | Gly | Gly |
| | 450 | | | | | 455 | | | | | 460 | | | | |
| Lys | Thr | Leu | Val | Glu | Tyr | Gln | Glu | Leu | Thr | Gly | Ala | Arg | Ile | Gln | Ile |
| 465 | | | | | 470 | | | | | 475 | | | | | 480 |
| Ser | Lys | Lys | Gly | Glu | Phe | Val | Pro | Gly | Thr | Arg | Asn | Arg | Lys | Val | Thr |
| | | | | 485 | | | | | 490 | | | | | 495 | |

| | | | | | | | | | | | | | |
|---|---|---|---|---|---|---|---|---|---|---|---|---|---|
| Ile | Thr | Gly | Thr<br>500 | Pro | Ala | Ala | Thr | Gln<br>505 | Ala | Ala | Gln | Tyr | Leu<br>510 | Ile | Thr |
| Gln | Arg | Ile<br>515 | Thr | Tyr | Glu | Gln | Gly<br>520 | Val | Arg | Ala | Ala | Asn<br>525 | Pro | Gln | Lys |
| Val | Gly<br>530 | | | | | | | | | | | | |

What is claimed is:

1. An Ri fusion protein which comprises an antigenic epitope that is recognized by autoantibodies from patients with paraneoplastic opsoclonus, said fusion protein having the amino acid sequence designated Sequence ID Numbers 2.

2. The Ri fusion protein of claim 1, labelled with a detectable marker.

3. The Ri fusion protein of claim 2, wherein the detectable marker is a radioisotope, dye, enzyme or biotin.

4. A method of detecting an antibody associated with paraneoplastic opsoclonus which comprises contacting a suit-able sample with the Ri fusion protein of claim 3 under conditions so as to form a complex between the Ri fusion protein and the antibody, detecting the presence of any complex so formed, and thereby detecting the antibody associated with paraneoplastic opsoclonus.

5. The method of claim 4, wherein the Ri fusion protein is labelled with a detectable marker.

6. The method of claim 5, wherein the detectable marker is a radioisotope, dye, enzyme or biotin.

* * * * *